(12) United States Patent
Matsuno et al.

(10) Patent No.: US 7,326,546 B2
(45) Date of Patent: Feb. 5, 2008

(54) PURINE-DERIVED SUBSTANCE-PRODUCING BACTERIUM AND A METHOD FOR PRODUCING PURINE-DERIVED SUBSTANCE

(75) Inventors: Kiyoshi Matsuno, Kawasaki (JP); Yukiko Mori, Kawasaki (JP); Takayuki Asahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/276,658

(22) Filed: Mar. 9, 2006

(65) Prior Publication Data
US 2006/0275874 A1 Dec. 7, 2006

(30) Foreign Application Priority Data
Mar. 10, 2005 (JP) ............... 2005-067560
Sep. 27, 2005 (JP) ............... 2005-280186

(51) Int. Cl.
 C12P 19/30 (2006.01)
 C12N 9/90 (2006.01)
 C12N 1/21 (2006.01)
(52) U.S. Cl. ........... 435/89; 435/233; 435/252.31; 536/23.2
(58) Field of Classification Search ............ None
See application file for complete search history.

(56) References Cited

U.S. PATENT DOCUMENTS

| | | | |
|---|---|---|---|
| 3,736,228 A | 5/1973 | Nakayama et al. |
| 3,912,587 A | 10/1975 | Enei et al. |
| 3,960,660 A | 6/1976 | Enei et al. |
| 3,960,661 A | 6/1976 | Enei et al. |
| 4,749,650 A | 6/1988 | Kenichiro et al. |
| 6,284,495 B1 | 9/2001 | Sato et al. |
| 2003/0068791 A1 | 4/2003 | Miasnikov et al. |
| 2004/0166570 A1 | 8/2004 | Asahara et al. |
| 2004/0166575 A1 | 8/2004 | Tominaga et al. |
| 2004/0171134 A1 | 9/2004 | Asahara et al. |
| 2004/0214296 A1 | 10/2004 | Asahara et al. |
| 2005/0003497 A1 | 1/2005 | Nishi et al. |
| 2006/0014259 A9 | 1/2006 | Burke et al. |

FOREIGN PATENT DOCUMENTS

| | | |
|---|---|---|
| EP | 0 273 660 | 7/1988 |
| EP | 0 286 303 | 10/1988 |
| EP | 0 393 969 | 10/1990 |
| EP | 0 412 688 | 2/1991 |
| EP | 0 465 132 | 1/1992 |
| EP | 1 004 663 | 5/2000 |
| JP | 51-5075 | 2/1976 |
| JP | 54-17033 | 6/1979 |
| JP | 55-2956 | 1/1980 |
| JP | 55-45199 | 11/1980 |
| JP | 58-158197 | 9/1983 |
| JP | 58-175493 | 10/1983 |
| JP | 59-028470 | 2/1984 |
| JP | 59-042895 | 3/1984 |
| JP | 60-156388 | 8/1985 |
| JP | 63-248394 | 10/1988 |
| JP | 64-027477 | 1/1989 |
| JP | 01-174385 | 7/1989 |
| JP | 03-058787 | 3/1991 |
| JP | 03-164185 | 7/1991 |
| JP | 05-084067 | 4/1993 |
| JP | 05-192164 | 8/1993 |
| WO | WO99/03988 | 1/1999 |
| WO | WO01/70995 | 9/2001 |
| WO | WO 2005/059154 | * 12/2004 |

OTHER PUBLICATIONS

Database WPI Week 200377, Derwent Publications Ltd., London, GB; AN 2003-819981.
DATABASE UniProt, Feb. 1, 1995, Glaser P et al: "Putative sugar phosphate isomerase ywlf (EC 5.3.1.-).", Database accession No. P39156.
DATABASE UniProt, Oct. 1, 1996, Mizuno M et al: "Glucose-6-phosphate 1-dehydrogenase (EC 1.1.1.49) (G6PD) (Vegetative protein 11) (VEG 11)", Database accession No. P54547.
Search Report for European Patent App. No. 06004995.4 (Feb. 5, 2007).
Flores, S., et al., "Growth-Rate Recovery of *Escherichia coli* Cultures Carrying a Multicopy Plasmid, by Engineering of the Pentose-Phosphate Pathway," Biotechnol. Bioeng. 2004;87(4):485-494.
Kamada, N., et al., "Significance of the non-oxidative route of the pentose phosphate pathway for supplying carbon to the purine-nucleotide pathway in *Corynebacterium ammoniagenes*," J. Ind. Microbiol. Biotechnol. 2003;30:129-132.
KEGG (Kyoto Encylcopedia of Genes and Genomes), Entry No. BG10942, *Bacillus subtilis*.
KEGG (Kyoto Encyclopedia of Genes and Genomes), Entry No. BG11739, *Bacillus subtilis*.
Lim, S-J, et al., "Amplification of the NADPH-Related Genes *zwf* and *gnd* for the Oddball Biosynthesis of PHB in an *E. coli* Transformant Harboring a Cloned *phbCAB* Operon," J. Biosci. Bioeng. 2002;93(6):543-549.
Tao, H., et al., "Engineering a Homo-Ethanol Pathway in *Escherichia coli*: Increased Glycolytic Flux and Levels of Expression of Glycolytic Genes during Xylose Fermentation," J. Bacteriol. 2001;183(10):2979-2988.

* cited by examiner

*Primary Examiner*—Rebecca E. Prouty
*Assistant Examiner*—Md. Younus Meah
(74) *Attorney, Agent, or Firm*—Shelly Guest Cermak; Cermak Kenealy & Vaidya LLP

(57) ABSTRACT

A purine-derived substance is produced by culturing a *Bacillus* bacterium which has an ability to produce a purine-derived substance and has enhanced activity of an enzyme of the oxidative pentosephosphate pathway. The purine-derived substance is produced in the medium or the bacterial cells, and can be collected from the medium or the bacterial cells.

12 Claims, 1 Drawing Sheet

Figure 1 tatcgttgacattatccatgtccgttgttaagataaacatgaaatcaaaac
      -35 sequence          -10 sequence
acgacctcatataatcttgggaatatggcccataagtttctacccggcaacc gtaaattgccggactatgcaggaaagtgatcgataaaactgacatggata tatcGCAGAAGCGAACGACTGACGATACATGTACC

ATGCCCGGTTTGTATTGCTTCCTCATAAGTGCAAT

GCAGAGCGGgtattttttattttctgaaaacaaaagcattagaaggt
                  → purE
ggggaacagaatgcagccgc

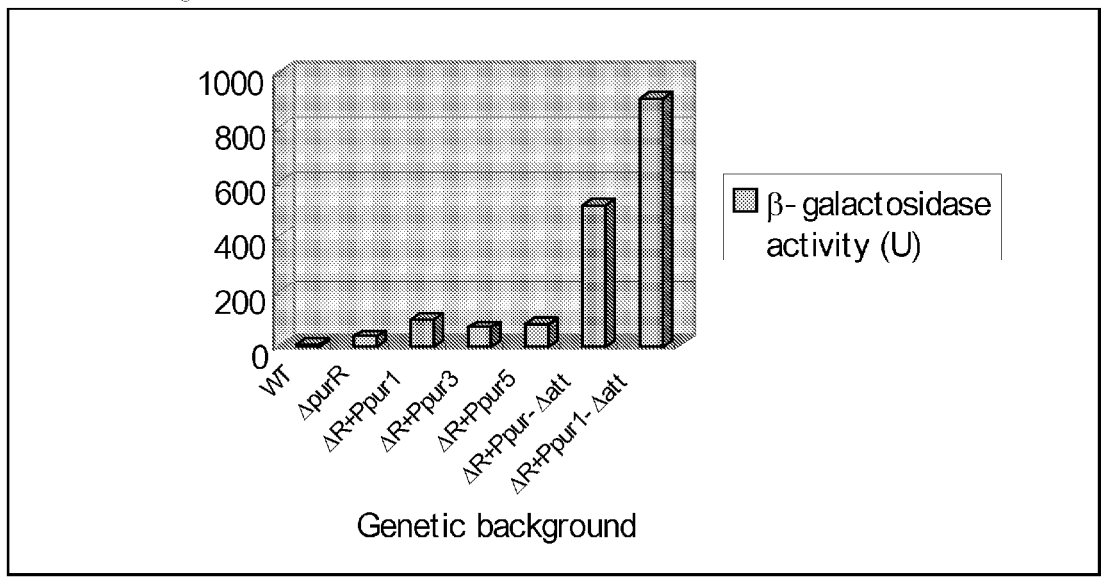

SEQUENCE LISTING

<160> NUMBER OF SEQ ID NOS: 62

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
attgcacggc cgttcgtcgg                    20

<210> SEQ ID NO 2
<211> LENGTH: 29
<212> TYPE: DNA
<213> ORGANISM: Artificial sequence
<220> FEATURE:
<223> OTHER INFORMATION: primer

<400> SEQUENCE: 2
cgcagatctc cggattttcg atttcgtcc          29

```
<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
caaagatctg tccagcctgg                                              20

<210> SEQ ID NO 4
<211> LENGTH: 29
<212> TYPE: DNA
<213> ORGANISM: Artificial sequence
<220> FEATURE:
<223> OTHER INFORMATION: primer

<400> SEQUENCE: 4
cgcctgcagt gcctttatct aaagcttcc                                    29

<210> SEQ ID NO 5
<211> LENGTH: 19
<212> TYPE: DNA
<213> ORGANISM: Artificial sequence
<220> FEATURE:
<223> OTHER INFORMATION: primer

<400> SEQUENCE: 5
ggtctgagct ttgcgaacc                                               19

<210> SEQ ID NO 6
<211> LENGTH: 29
<212> TYPE: DNA
<213> ORGANISM: Artificial sequence
<220> FEATURE:
<223> OTHER INFORMATION: primer

<400> SEQUENCE: 6
cgcctgcagt gcctttatct aaagcttcc                                    29

<210> SEQ ID NO 7
<211> LENGTH: 34
<212> TYPE: DNA
<213> ORGANISM: Artificial sequence
<220> FEATURE:
<223> OTHER INFORMATION: primer

<400> SEQUENCE: 7
cgcggatccg gcttaacgtt cgacgatgtg ctgc                              34

<210> SEQ ID NO 8
<211> LENGTH: 50
<212> TYPE: DNA
<213> ORGANISM: Artificial sequence
<220> FEATURE:
<223> OTHER INFORMATION: primer

<400> SEQUENCE: 8
gctttgccca ttctatagat atattgagtc attgtatcgc cagttacacc             50

<210> SEQ ID NO 9
<211> LENGTH: 50
<212> TYPE: DNA
<213> ORGANISM: Artificial sequence
<220> FEATURE:
<223> OTHER INFORMATION: primer
```

```
<400> SEQUENCE: 9
cctagattta gatgtctaaa aagctgtgat tgttatcgat acagctcacg          50

<210> SEQ ID NO 10
<211> LENGTH: 34
<212> TYPE: DNA
<213> ORGANISM: Artificial sequence
<220> FEATURE:
<223> OTHER INFORMATION: primer

<400> SEQUENCE: 10
cgcgaattcg taatctgtac gtcatgcgga tggc                          34

<210> SEQ ID NO 11
<211> LENGTH: 50
<212> TYPE: DNA
<213> ORGANISM: Artificial sequence
<220> FEATURE:
<223> OTHER INFORMATION: primer

<400> SEQUENCE: 11
ggtgtaactg gcgatacaat gactcaatat atctatagaa tgggcaaagc          50

<210> SEQ ID NO 12
<211> LENGTH: 50
<212> TYPE: DNA
<213> ORGANISM: Artificial sequence
<220> FEATURE:
<223> OTHER INFORMATION: primer

<400> SEQUENCE: 12
cgtgagctgt atcgataaca atcacagctt tttagacatc taaatctagg          50

<210> SEQ ID NO 13
<211> LENGTH: 25
<212> TYPE: DNA
<213> ORGANISM: Artificial sequence
<220> FEATURE:
<223> OTHER INFORMATION: primer

<400> SEQUENCE: 13
cataaaatgt acgcataggc cattc                                    25

<210> SEQ ID NO 14
<211> LENGTH: 46
<212> TYPE: DNA
<213> ORGANISM: Artificial sequence
<220> FEATURE:
<223> OTHER INFORMATION: primer

<400> SEQUENCE: 14
ttgtatcgcc agttacacca actaccgcgc caacgatcag gcggcc              46

<210> SEQ ID NO 15
<211> LENGTH: 46
<212> TYPE: DNA
<213> ORGANISM: Artificial sequence
<220> FEATURE:
<223> OTHER INFORMATION: primer

<400> SEQUENCE: 15
ggccgcctga tcgttggcgc ggtagttggt gtaactggcg atacaa              46

<210> SEQ ID NO 16
<211> LENGTH: 26
```

```
<212> TYPE: DNA
<213> ORGANISM: Artificial sequence
<220> FEATURE:
<223> OTHER INFORMATION: primer

<400> SEQUENCE: 16
ccttgatcaa ttgcttccaa taacag                                          26

<210> SEQ ID NO 17
<211> LENGTH: 34
<212> TYPE: DNA
<213> ORGANISM: Artificial sequence
<220> FEATURE:
<223> OTHER INFORMATION: primer

<400> SEQUENCE: 17
cgcggatcct tatttagcgg ccggcatcag tacg                                 34

<210> SEQ ID NO 18
<211> LENGTH: 50
<212> TYPE: DNA
<213> ORGANISM: Artificial sequence
<220> FEATURE:
<223> OTHER INFORMATION: primer

<400> SEQUENCE: 18
cgtttgttga actaatgggt gctttatgga taatgtcaac gatattatcg                50

<210> SEQ ID NO 19
<211> LENGTH: 50
<212> TYPE: DNA
<213> ORGANISM: Artificial sequence
<220> FEATURE:
<223> OTHER INFORMATION: primer

<400> SEQUENCE: 19
acagctccag atccatatcc ttcttcctca tataatcttg ggaatatggc                50

<210> SEQ ID NO 20
<211> LENGTH: 34
<212> TYPE: DNA
<213> ORGANISM: Artificial sequence
<220> FEATURE:
<223> OTHER INFORMATION: primer

<400> SEQUENCE: 20
cgcggatcct ctctcatcca gcttacgggc aagg                                 34

<210> SEQ ID NO 21
<211> LENGTH: 50
<212> TYPE: DNA
<213> ORGANISM: Artificial sequence
<220> FEATURE:
<223> OTHER INFORMATION: primer

<400> SEQUENCE: 21
cgataatatc gttgacatta tccataaagc acccattagt tcaacaaacg                50

<210> SEQ ID NO 22
<211> LENGTH: 50
<212> TYPE: DNA
<213> ORGANISM: Artificial sequence
<220> FEATURE:
<223> OTHER INFORMATION: primer

<400> SEQUENCE: 22
```
gccatattcc caagattata tgaggaagaa ggatatggat ctggagctgt         50

<210> SEQ ID NO 23
<211> LENGTH: 38
<212> TYPE: DNA
<213> ORGANISM: Artificial sequence
<220> FEATURE:
<223> OTHER INFORMATION: primer

<400> SEQUENCE: 23
ttttgatttc atgtttatta taacaacgga catggata                     38

<210> SEQ ID NO 24
<211> LENGTH: 38
<212> TYPE: DNA
<213> ORGANISM: Artificial sequence
<220> FEATURE:
<223> OTHER INFORMATION: primer

<400> SEQUENCE: 24
ttttgatttc atgtttatca taacaacgga catggata                     38

<210> SEQ ID NO 25
<211> LENGTH: 38
<212> TYPE: DNA
<213> ORGANISM: Artificial sequence
<220> FEATURE:
<223> OTHER INFORMATION: primer

<400> SEQUENCE: 25
ttttgatttc atgtttattt taacaacgga catggata                     38

<210> SEQ ID NO 26
<211> LENGTH: 25
<212> TYPE: DNA
<213> ORGANISM: Artificial sequence
<220> FEATURE:
<223> OTHER INFORMATION: primer

<400> SEQUENCE: 26
gggtaataag cagcagctca cttcc                                   25

<210> SEQ ID NO 27
<211> LENGTH: 38
<212> TYPE: DNA
<213> ORGANISM: Artificial sequence
<220> FEATURE:
<223> OTHER INFORMATION: primer

<400> SEQUENCE: 27
tatccatgtc cgttgttata ataaacatga aatcaaaa                     38

<210> SEQ ID NO 28
<211> LENGTH: 38
<212> TYPE: DNA
<213> ORGANISM: Artificial sequence
<220> FEATURE:
<223> OTHER INFORMATION: primer

<400> SEQUENCE: 28
tatccatgtc cgttgttatg ataaacatga aatcaaaa                     38

<210> SEQ ID NO 29
<211> LENGTH: 38
<212> TYPE: DNA
<213> ORGANISM: Artificial sequence

```
<220> FEATURE:
<223> OTHER INFORMATION: primer

<400> SEQUENCE: 29
tatccatgtc cgttgttaaa ataaacatga aatcaaaa                              38

<210> SEQ ID NO 30
<211> LENGTH: 52
<212> TYPE: DNA
<213> ORGANISM: Artificial sequence
<220> FEATURE:
<223> OTHER INFORMATION: primer

<400> SEQUENCE: 30
gcttttgttt tcagaaaata aaaatacga tatatccatg tcagttttat cg              52

<210> SEQ ID NO 31
<211> LENGTH: 52
<212> TYPE: DNA
<213> ORGANISM: Artificial sequence
<220> FEATURE:
<223> OTHER INFORMATION: primer

<400> SEQUENCE: 31
cgataaaact gacatggata tatcgtattt tttattttct gaaaacaaaa gc              52

<210> SEQ ID NO 32
<211> LENGTH: 29
<212> TYPE: DNA
<213> ORGANISM: Artificial sequence
<220> FEATURE:
<223> OTHER INFORMATION: primer

<400> SEQUENCE: 32
cgcaagcttt attttctgaa aacaaaagc                                        29

<210> SEQ ID NO 33
<211> LENGTH: 29
<212> TYPE: DNA
<213> ORGANISM: Artificial sequence
<220> FEATURE:
<223> OTHER INFORMATION: primer

<400> SEQUENCE: 33
cgcggatcct ttctcttctc tcatccagc                                        29

<210> SEQ ID NO 34
<211> LENGTH: 34
<212> TYPE: DNA
<213> ORGANISM: Artificial sequence
<220> FEATURE:
<223> OTHER INFORMATION: primer

<400> SEQUENCE: 34
cgcggatcca acatacacaa agagaagcga aagc                                  34

<210> SEQ ID NO 35
<211> LENGTH: 46
<212> TYPE: DNA
<213> ORGANISM: Artificial sequence
<220> FEATURE:
<223> OTHER INFORMATION: primer

<400> SEQUENCE: 35
gattagacat ggataaacct ccttatttag gattattttt tatgaa                    46
```

<210> SEQ ID NO 36
<211> LENGTH: 46
<212> TYPE: DNA
<213> ORGANISM: Artificial sequence
<220> FEATURE:
<223> OTHER INFORMATION: primer

<400> SEQUENCE: 36
gattagacat ggataaacct cctaatttag gattattttt tatgaa         46

<210> SEQ ID NO 37
<211> LENGTH: 46
<212> TYPE: DNA
<213> ORGANISM: Artificial sequence
<220> FEATURE:
<223> OTHER INFORMATION: primer

<400> SEQUENCE: 37
gattagacat ggataaacct ccgtatttag gattattttt tatgaa         46

<210> SEQ ID NO 38
<211> LENGTH: 40
<212> TYPE: DNA
<213> ORGANISM: Artificial sequence
<220> FEATURE:
<223> OTHER INFORMATION: primer

<400> SEQUENCE: 38
cgcggatccg gtttagctga acagatagct gactgattgc                40

<210> SEQ ID NO 39
<211> LENGTH: 46
<212> TYPE: DNA
<213> ORGANISM: Artificial sequence
<220> FEATURE:
<223> OTHER INFORMATION: primer

<400> SEQUENCE: 39
ttcataaaaa ataatcctaa ataaggaggt ttatccatgt ctaatc         46

<210> SEQ ID NO 40
<211> LENGTH: 46
<212> TYPE: DNA
<213> ORGANISM: Artificial sequence
<220> FEATURE:
<223> OTHER INFORMATION: primer

<400> SEQUENCE: 40
ttcataaaaa ataatcctaa attaggaggt ttatccatgt ctaatc         46

<210> SEQ ID NO 41
<211> LENGTH: 46
<212> TYPE: DNA
<213> ORGANISM: Artificial sequence
<220> FEATURE:
<223> OTHER INFORMATION: primer

<400> SEQUENCE: 41
ttcataaaaa ataatcctaa atacggaggt ttatccatgt ctaatc         46

<210> SEQ ID NO 42
<211> LENGTH: 25
<212> TYPE: DNA
<213> ORGANISM: Artificial sequence
<220> FEATURE:
<223> OTHER INFORMATION: primer

<400> SEQUENCE: 42
aatagatata aagaggtgag tctgc                                     25

<210> SEQ ID NO 43
<211> LENGTH: 29
<212> TYPE: DNA
<213> ORGANISM: Artificial sequence
<220> FEATURE:
<223> OTHER INFORMATION: primer

<400> SEQUENCE: 43
cgcggatccg cctctgaaaa gaacaatcc                                 29

<210> SEQ ID NO 44
<211> LENGTH: 29
<212> TYPE: DNA
<213> ORGANISM: Artificial sequence
<220> FEATURE:
<223> OTHER INFORMATION: primer

<400> SEQUENCE: 44
cgcggatcca agctcttaag ctttgggggg                                29

<210> SEQ ID NO 45
<211> LENGTH: 34
<212> TYPE: DNA
<213> ORGANISM: Artificial sequence
<220> FEATURE:
<223> OTHER INFORMATION: primer

<400> SEQUENCE: 45
cgcgaattcg tagataagtt gtcagaaaat ctgc                           34

<210> SEQ ID NO 46
<211> LENGTH: 34
<212> TYPE: DNA
<213> ORGANISM: Artificial sequence
<220> FEATURE:
<223> OTHER INFORMATION: primer

<400> SEQUENCE: 46
cgcgaattct gtttcaactc attcattaaa cagc                           34

<210> SEQ ID NO 47
<211> LENGTH: 1470
<212> TYPE: DNA
<213> ORGANISM: Bacillus subtilis
<220> FEATURE:
<221> NAME/KEY: CDS
<222> LOCATION: (1)..(1470)

<400> SEQUENCE: 47

| gtg | aaa | aca | aac | caa | caa | cca | aaa | gca | gta | att | gtc | ata | ttc | ggt | gca | 48 |
| Met | Lys | Thr | Asn | Gln | Gln | Pro | Lys | Ala | Val | Ile | Val | Ile | Phe | Gly | Ala | |
| 1 | | | | 5 | | | | | 10 | | | | | 15 | | |

| act | gga | gat | tta | gca | aaa | cga | aaa | ttg | tat | ccg | tct | att | cac | cgt | tta | 96 |
| Thr | Gly | Asp | Leu | Ala | Lys | Arg | Lys | Leu | Tyr | Pro | Ser | Ile | His | Arg | Leu | |
| | | | 20 | | | | | 25 | | | | | 30 | | | |

| tat | caa | aac | gga | caa | atc | gga | gaa | gag | ttt | gca | gtg | gta | gga | gtt | gga | 144 |
| Tyr | Gln | Asn | Gly | Gln | Ile | Gly | Glu | Glu | Phe | Ala | Val | Val | Gly | Val | Gly | |
| | | 35 | | | | | 40 | | | | | 45 | | | | |

| aga | aga | cct | tgg | tct | aat | gag | gat | ctt | cgc | caa | act | gtt | aaa | aca | tcc | 192 |
| Arg | Arg | Pro | Trp | Ser | Asn | Glu | Asp | Leu | Arg | Gln | Thr | Val | Lys | Thr | Ser | |
| 50 | | | | | 55 | | | | | 60 | | | | | | |

-continued

```
att tcc tca tct gca gat aag cat ata gat gat ttc acg tct cat ttt       240
Ile Ser Ser Ser Ala Asp Lys His Ile Asp Asp Phe Thr Ser His Phe
 65                  70                  75                  80 tac tat cac ccg ttt gac gtg aca aac cct ggt tct tat caa gag cta       288
Tyr Tyr His Pro Phe Asp Val Thr Asn Pro Gly Ser Tyr Gln Glu Leu
                 85                  90                  95 aac gta ttg ctt aac cag ctg gaa gat aca tat caa att cct aac aac       336
Asn Val Leu Leu Asn Gln Leu Glu Asp Thr Tyr Gln Ile Pro Asn Asn
            100                 105                 110 aga atg ttc tac ttg gca atg gct cct gaa ttc ttc gga acg att gca       384
Arg Met Phe Tyr Leu Ala Met Ala Pro Glu Phe Phe Gly Thr Ile Ala
        115                 120                 125 aaa aca tta aaa tca gag ggt gta aca gct aca acc ggc tgg tcc cgc       432
Lys Thr Leu Lys Ser Glu Gly Val Thr Ala Thr Thr Gly Trp Ser Arg
130                 135                 140 ctt gtc atc gaa aaa ccg ttc ggc cat gat ctg cca agc gca cag gca       480
Leu Val Ile Glu Lys Pro Phe Gly His Asp Leu Pro Ser Ala Gln Ala
145                 150                 155                 160 ttg aat aaa gaa atc cgc gaa gca ttt acg gaa gat caa att tac aga       528
Leu Asn Lys Glu Ile Arg Glu Ala Phe Thr Glu Asp Gln Ile Tyr Arg
                165                 170                 175 atc gac cat tat cta ggc aaa caa atg gtt cag aac att gaa gtg att       576
Ile Asp His Tyr Leu Gly Lys Gln Met Val Gln Asn Ile Glu Val Ile
            180                 185                 190 cga ttt gcc aat gcg att ttc gaa ccg ctt tgg aca aac cgc tac att       624
Arg Phe Ala Asn Ala Ile Phe Glu Pro Leu Trp Thr Asn Arg Tyr Ile
        195                 200                 205 tca aac att caa atc aca tct agc gaa tca cta ggc gtt gaa gac cgc       672
Ser Asn Ile Gln Ile Thr Ser Ser Glu Ser Leu Gly Val Glu Asp Arg
    210                 215                 220 gca aga tat tac gaa aaa tca ggc gcc ctt cgc gac atg gtg caa aac       720
Ala Arg Tyr Tyr Glu Lys Ser Gly Ala Leu Arg Asp Met Val Gln Asn
225                 230                 235                 240 cat att atg cag atg gtt gcc ctt ctt gca atg gag ccg cct atc aaa       768
His Ile Met Gln Met Val Ala Leu Leu Ala Met Glu Pro Pro Ile Lys
                245                 250                 255 ttg aac aca gaa gaa atc cgc agc gag aaa gtg aag gtg ctg aga gca       816
Leu Asn Thr Glu Glu Ile Arg Ser Glu Lys Val Lys Val Leu Arg Ala
            260                 265                 270 ctg cgt cct att gca aaa gac gaa gtg gat gaa tac ttt gtg cgc gga       864
Leu Arg Pro Ile Ala Lys Asp Glu Val Asp Glu Tyr Phe Val Arg Gly
        275                 280                 285 caa tat cat gct ggt gaa att gac ggt gta ccg gtt cct gct tat aca       912
Gln Tyr His Ala Gly Glu Ile Asp Gly Val Pro Val Pro Ala Tyr Thr
    290                 295                 300 gat gaa gat aat gtc gct cct gac tcc aat aca gaa acc ttt gtt gcc       960
Asp Glu Asp Asn Val Ala Pro Asp Ser Asn Thr Glu Thr Phe Val Ala
305                 310                 315                 320 ggc aag ctc ttg atc gac aac ttc aga tgg gct ggt gtt cca ttc tac      1008
Gly Lys Leu Leu Ile Asp Asn Phe Arg Trp Ala Gly Val Pro Phe Tyr
                325                 330                 335 atc aga acc gga aaa cga atg aga gaa aag tcc aca aaa att gtc gtt      1056
Ile Arg Thr Gly Lys Arg Met Arg Glu Lys Ser Thr Lys Ile Val Val
            340                 345                 350 caa ttt aag gac att ccg atg aac ctg tac tac ggt aat gaa aac aac      1104
Gln Phe Lys Asp Ile Pro Met Asn Leu Tyr Tyr Gly Asn Glu Asn Asn
        355                 360                 365 atg aat ccg aac ttg ctt gtc att cat att cag cct gac gaa ggc att      1152
Met Asn Pro Asn Leu Leu Val Ile His Ile Gln Pro Asp Glu Gly Ile
```

-continued

```
                    370                 375                 380
acg ctt tac tta aat gct aaa aag ctt ggc gga gca gca cac gca cag      1200
Thr Leu Tyr Leu Asn Ala Lys Lys Leu Gly Gly Ala Ala His Ala Gln
385                 390                 395                 400 cca atc aaa ctc gat tat tgc agc aat tgc aat gac gag ttg aac acc      1248
Pro Ile Lys Leu Asp Tyr Cys Ser Asn Cys Asn Asp Glu Leu Asn Thr
                405                 410                 415 cct gaa gca tat gaa aaa cta att cac gac tgt ctt ctt ggc gat gca      1296
Pro Glu Ala Tyr Glu Lys Leu Ile His Asp Cys Leu Leu Gly Asp Ala
            420                 425                 430 aca aac ttt gca cac tgg gat gaa gtt gcc ctt tct tgg agc ttt gtc      1344
Thr Asn Phe Ala His Trp Asp Glu Val Ala Leu Ser Trp Ser Phe Val
        435                 440                 445 gac tct att tct gaa aca tgg gca gca aac aaa acc tta tct cct aac      1392
Asp Ser Ile Ser Glu Thr Trp Ala Ala Asn Lys Thr Leu Ser Pro Asn
    450                 455                 460 tac gaa tca ggc tca atg gga ccg aaa gaa tct gat gat ctt ttg gtg      1440
Tyr Glu Ser Gly Ser Met Gly Pro Lys Glu Ser Asp Asp Leu Leu Val
465                 470                 475                 480 aaa gac ggc tta cac tgg tgg aac ata taa                              1470
Lys Asp Gly Leu His Trp Trp Asn Ile
                485
```

<210> SEQ ID NO 48
<211> LENGTH: 489
<212> TYPE: PRT
<213> ORGANISM: Bacillus subtilis

<400> SEQUENCE: 48

```
Met Lys Thr Asn Gln Gln Pro Lys Ala Val Ile Val Ile Phe Gly Ala
1               5                   10                  15

Thr Gly Asp Leu Ala Lys Arg Lys Leu Tyr Pro Ser Ile His Arg Leu
            20                  25                  30

Tyr Gln Asn Gly Gln Ile Gly Glu Glu Phe Ala Val Val Gly Val Gly
        35                  40                  45

Arg Arg Pro Trp Ser Asn Glu Asp Leu Arg Gln Thr Val Lys Thr Ser
    50                  55                  60

Ile Ser Ser Ala Asp Lys His Ile Asp Asp Phe Thr Ser His Phe
65                  70                  75                  80

Tyr Tyr His Pro Phe Asp Val Thr Asn Pro Gly Ser Tyr Gln Glu Leu
                85                  90                  95

Asn Val Leu Leu Asn Gln Leu Glu Asp Thr Tyr Gln Ile Pro Asn Asn
            100                 105                 110

Arg Met Phe Tyr Leu Ala Met Ala Pro Glu Phe Phe Gly Thr Ile Ala
        115                 120                 125

Lys Thr Leu Lys Ser Glu Gly Val Thr Ala Thr Thr Gly Trp Ser Arg
    130                 135                 140

Leu Val Ile Glu Lys Pro Phe Gly His Asp Leu Pro Ser Ala Gln Ala
145                 150                 155                 160

Leu Asn Lys Glu Ile Arg Glu Ala Phe Thr Glu Asp Gln Ile Tyr Arg
                165                 170                 175

Ile Asp His Tyr Leu Gly Lys Gln Met Val Gln Asn Ile Glu Val Ile
            180                 185                 190

Arg Phe Ala Asn Ala Ile Phe Glu Pro Leu Trp Thr Asn Arg Tyr Ile
        195                 200                 205

Ser Asn Ile Gln Ile Thr Ser Ser Glu Ser Leu Gly Val Glu Asp Arg
    210                 215                 220
```

```
Ala Arg Tyr Tyr Glu Lys Ser Gly Ala Leu Arg Asp Met Val Gln Asn
225                 230                 235                 240

His Ile Met Gln Met Val Ala Leu Leu Ala Met Glu Pro Pro Ile Lys
            245                 250                 255

Leu Asn Thr Glu Glu Ile Arg Ser Glu Lys Val Lys Val Leu Arg Ala
            260                 265                 270

Leu Arg Pro Ile Ala Lys Asp Glu Val Asp Tyr Phe Val Arg Gly
            275                 280                 285

Gln Tyr His Ala Gly Glu Ile Asp Gly Val Pro Val Pro Ala Tyr Thr
290                 295                 300

Asp Glu Asp Asn Val Ala Pro Asp Ser Asn Thr Glu Thr Phe Val Ala
305                 310                 315                 320

Gly Lys Leu Leu Ile Asp Asn Phe Arg Trp Ala Gly Val Pro Phe Tyr
                325                 330                 335

Ile Arg Thr Gly Lys Arg Met Arg Glu Lys Ser Thr Lys Ile Val Val
            340                 345                 350

Gln Phe Lys Asp Ile Pro Met Asn Leu Tyr Tyr Gly Asn Glu Asn Asn
        355                 360                 365

Met Asn Pro Asn Leu Leu Val Ile His Ile Gln Pro Asp Glu Gly Ile
    370                 375                 380

Thr Leu Tyr Leu Asn Ala Lys Lys Leu Gly Ala Ala His Ala Gln
385                 390                 395                 400

Pro Ile Lys Leu Asp Tyr Cys Ser Asn Cys Asn Asp Glu Leu Asn Thr
                405                 410                 415

Pro Glu Ala Tyr Glu Lys Leu Ile His Asp Cys Leu Leu Gly Asp Ala
            420                 425                 430

Thr Asn Phe Ala His Trp Asp Glu Val Ala Leu Ser Trp Ser Phe Val
        435                 440                 445

Asp Ser Ile Ser Glu Thr Trp Ala Ala Asn Lys Thr Leu Ser Pro Asn
450                 455                 460

Tyr Glu Ser Gly Ser Met Gly Pro Lys Glu Ser Asp Asp Leu Leu Val
465                 470                 475                 480

Lys Asp Gly Leu His Trp Trp Asn Ile
                485

<210> SEQ ID NO 49
<211> LENGTH: 450
<212> TYPE: DNA
<213> ORGANISM: Bacillus subtilis
<220> FEATURE:
<221> NAME/KEY: CDS
<222> LOCATION: (1)..(450)

<400> SEQUENCE: 49 atg aaa gta gcc att gca tcg gat cat ggc ggc gtt cac att cga aat       48
Met Lys Val Ala Ile Ala Ser Asp His Gly Gly Val His Ile Arg Asn
1               5                   10                  15 gaa atc aaa gag tta atg gac gaa ttg caa att gaa tat att gat atg       96
Glu Ile Lys Glu Leu Met Asp Glu Leu Gln Ile Glu Tyr Ile Asp Met
            20                  25                  30 ggc tgt gac tgc ggc agc ggc tct gtc gat tat ccg gat tat gct ttt      144
Gly Cys Asp Cys Gly Ser Gly Ser Val Asp Tyr Pro Asp Tyr Ala Phe
        35                  40                  45 ccg gtg gcc gaa aaa gtg gtt agc ggc gaa gtt gac aga ggc att tta      192
Pro Val Ala Glu Lys Val Val Ser Gly Glu Val Asp Arg Gly Ile Leu
    50                  55                  60
```

```
att tgc ggg aca ggc atc ggc atg agc att tcc gct aat aaa gta aaa      240
Ile Cys Gly Thr Gly Ile Gly Met Ser Ile Ser Ala Asn Lys Val Lys
65                  70                  75                  80 ggg att cgc tgc gcg ctg gca cac gat acc ttc agc gcg aag gcg acg      288
Gly Ile Arg Cys Ala Leu Ala His Asp Thr Phe Ser Ala Lys Ala Thr
                85                  90                  95 agg gag cat aat gac aca aac atc ctt gcg atg ggt gaa cgg gtg atc      336
Arg Glu His Asn Asp Thr Asn Ile Leu Ala Met Gly Glu Arg Val Ile
            100                 105                 110 gga cct ggt ttg gct cgg gaa atc gca aaa atc tgg ctg act act gag      384
Gly Pro Gly Leu Ala Arg Glu Ile Ala Lys Ile Trp Leu Thr Thr Glu
        115                 120                 125 ttt acc ggg gga aga cac caa acg cgt att gga aaa atc tcc gat tat      432
Phe Thr Gly Gly Arg His Gln Thr Arg Ile Gly Lys Ile Ser Asp Tyr
    130                 135                 140 gaa gag aaa aac ctg tag                                              450
Glu Glu Lys Asn Leu
145
```

<210> SEQ ID NO 50
<211> LENGTH: 149
<212> TYPE: PRT
<213> ORGANISM: Bacillus subtilis

<400> SEQUENCE: 50

```
Met Lys Val Ala Ile Ala Ser Asp His Gly Gly Val His Ile Arg Asn
1               5                   10                  15

Glu Ile Lys Glu Leu Met Asp Glu Leu Gln Ile Glu Tyr Ile Asp Met
            20                  25                  30

Gly Cys Asp Cys Gly Ser Gly Ser Val Asp Tyr Pro Asp Tyr Ala Phe
        35                  40                  45

Pro Val Ala Glu Lys Val Val Ser Gly Glu Val Asp Arg Gly Ile Leu
    50                  55                  60

Ile Cys Gly Thr Gly Ile Gly Met Ser Ile Ser Ala Asn Lys Val Lys
65                  70                  75                  80

Gly Ile Arg Cys Ala Leu Ala His Asp Thr Phe Ser Ala Lys Ala Thr
                85                  90                  95

Arg Glu His Asn Asp Thr Asn Ile Leu Ala Met Gly Glu Arg Val Ile
            100                 105                 110

Gly Pro Gly Leu Ala Arg Glu Ile Ala Lys Ile Trp Leu Thr Thr Glu
        115                 120                 125

Phe Thr Gly Gly Arg His Gln Thr Arg Ile Gly Lys Ile Ser Asp Tyr
    130                 135                 140

Glu Glu Lys Asn Leu
145
```

<210> SEQ ID NO 51
<211> LENGTH: 858
<212> TYPE: DNA
<213> ORGANISM: Bacillus subtilis
<220> FEATURE:
<221> NAME/KEY: CDS
<222> LOCATION: (1)..(858)

<400> SEQUENCE: 51

```
atg aag ttt cgt cgc agc ggc aga ttg gtg gac tta aca aat tat ttg       48
Met Lys Phe Arg Arg Ser Gly Arg Leu Val Asp Leu Thr Asn Tyr Leu
1               5                   10                  15 tta acc cat ccg cac gag tta ata ccg cta acc ttt ttc tct gag cgg       96
Leu Thr His Pro His Glu Leu Ile Pro Leu Thr Phe Phe Ser Glu Arg
```

```
                20                  25                  30
tat gaa tct gca aaa tca tcg atc agt gaa gat tta aca att att aaa       144
Tyr Glu Ser Ala Lys Ser Ser Ile Ser Glu Asp Leu Thr Ile Ile Lys
        35                  40                  45 caa acc ttt gaa cag cag ggg att ggt act ttg ctt act gtt ccc gga       192
Gln Thr Phe Glu Gln Gln Gly Ile Gly Thr Leu Leu Thr Val Pro Gly
    50                  55                  60 gct gcc gga ggc gtt aaa tat att ccg aaa atg aag cag gct gaa gct       240
Ala Ala Gly Gly Val Lys Tyr Ile Pro Lys Met Lys Gln Ala Glu Ala
65                  70                  75                  80 gaa gag ttt gtg cag aca ctt gga cag tcg ctg gca aat cct gag cgt       288
Glu Glu Phe Val Gln Thr Leu Gly Gln Ser Leu Ala Asn Pro Glu Arg
                85                  90                  95 atc ctt ccg ggc ggt tat gta tat tta acg gat atc tta gga aag cca       336
Ile Leu Pro Gly Gly Tyr Val Tyr Leu Thr Asp Ile Leu Gly Lys Pro
            100                 105                 110 tct gta ctc tcc aag gta ggg aag ctg ttt gct tcc gtg ttt gca gag       384
Ser Val Leu Ser Lys Val Gly Lys Leu Phe Ala Ser Val Phe Ala Glu
        115                 120                 125 cgc gaa att gat gtt gtc atg acc gtt gcc acg aaa ggc atc cct ctt       432
Arg Glu Ile Asp Val Val Met Thr Val Ala Thr Lys Gly Ile Pro Leu
    130                 135                 140 gcg tac gca gct gca agc tat ttg aat gtg cct gtt gtg atc gtt cgt       480
Ala Tyr Ala Ala Ala Ser Tyr Leu Asn Val Pro Val Val Ile Val Arg
145                 150                 155                 160 aaa gac aat aag gta aca gag ggc tcc aca gtc agc att aat tac gtt       528
Lys Asp Asn Lys Val Thr Glu Gly Ser Thr Val Ser Ile Asn Tyr Val
                165                 170                 175 tca ggc tcc tca aac cgc att caa aca atg tca ctt gcg aaa aga agc       576
Ser Gly Ser Ser Asn Arg Ile Gln Thr Met Ser Leu Ala Lys Arg Ser
            180                 185                 190 atg aaa acg ggt tca aac gta ctc att att gat gac ttt atg aaa gca       624
Met Lys Thr Gly Ser Asn Val Leu Ile Ile Asp Asp Phe Met Lys Ala
        195                 200                 205 ggc ggc acc att aat ggt atg att aac ctg ttg gat gag ttt aac gca       672
Gly Gly Thr Ile Asn Gly Met Ile Asn Leu Leu Asp Glu Phe Asn Ala
    210                 215                 220 aat gtg gcg gga atc ggc gtc tta gtt gaa gcc gaa gga gta gat gaa       720
Asn Val Ala Gly Ile Gly Val Leu Val Glu Ala Glu Gly Val Asp Glu
225                 230                 235                 240 cgt ctt gtt gac gaa tat atg tca ctt ctt act ctt tca acc atc aac       768
Arg Leu Val Asp Glu Tyr Met Ser Leu Leu Thr Leu Ser Thr Ile Asn
                245                 250                 255 atg aaa gag aag tcc att gaa att cag aat ggc aat ttt ctg cgt ttt       816
Met Lys Glu Lys Ser Ile Glu Ile Gln Asn Gly Asn Phe Leu Arg Phe
            260                 265                 270 ttt aaa gac aat ctt tta aag aat gga gag aca gaa tca tga              858
Phe Lys Asp Asn Leu Leu Lys Asn Gly Glu Thr Glu Ser
        275                 280                 285

<210> SEQ ID NO 52
<211> LENGTH: 285
<212> TYPE: PRT
<213> ORGANISM: Bacillus subtilis

<400> SEQUENCE: 52

Met Lys Phe Arg Arg Ser Gly Arg Leu Val Asp Leu Thr Asn Tyr Leu
1               5                   10                  15

Leu Thr His Pro His Glu Leu Ile Pro Leu Thr Phe Phe Ser Glu Arg
            20                  25                  30
```

```
Tyr Glu Ser Ala Lys Ser Ser Ile Ser Glu Asp Leu Thr Ile Ile Lys
            35                  40                  45

Gln Thr Phe Glu Gln Gln Gly Ile Gly Thr Leu Leu Thr Val Pro Gly
        50                  55                  60

Ala Ala Gly Gly Val Lys Tyr Ile Pro Lys Met Lys Gln Ala Glu Ala
65                  70                  75                  80

Glu Glu Phe Val Gln Thr Leu Gly Gln Ser Leu Ala Asn Pro Glu Arg
                85                  90                  95

Ile Leu Pro Gly Gly Tyr Val Tyr Leu Thr Asp Ile Leu Gly Lys Pro
                100                 105                 110

Ser Val Leu Ser Lys Val Gly Lys Leu Phe Ala Ser Val Phe Ala Glu
            115                 120                 125

Arg Glu Ile Asp Val Val Met Thr Val Ala Thr Lys Gly Ile Pro Leu
        130                 135                 140

Ala Tyr Ala Ala Ala Ser Tyr Leu Asn Val Pro Val Val Ile Val Arg
145                 150                 155                 160

Lys Asp Asn Lys Val Thr Glu Gly Ser Thr Val Ser Ile Asn Tyr Val
                165                 170                 175

Ser Gly Ser Ser Asn Arg Ile Gln Thr Met Ser Leu Ala Lys Arg Ser
                180                 185                 190

Met Lys Thr Gly Ser Asn Val Leu Ile Ile Asp Asp Phe Met Lys Ala
            195                 200                 205

Gly Gly Thr Ile Asn Gly Met Ile Asn Leu Leu Asp Glu Phe Asn Ala
        210                 215                 220

Asn Val Ala Gly Ile Gly Val Leu Val Glu Ala Glu Gly Val Asp Glu
225                 230                 235                 240

Arg Leu Val Asp Glu Tyr Met Ser Leu Leu Thr Leu Ser Thr Ile Asn
                245                 250                 255

Met Lys Glu Lys Ser Ile Glu Ile Gln Asn Gly Asn Phe Leu Arg Phe
            260                 265                 270

Phe Lys Asp Asn Leu Leu Lys Asn Gly Glu Thr Glu Ser
        275                 280                 285

<210> SEQ ID NO 53
<211> LENGTH: 816
<212> TYPE: DNA
<213> ORGANISM: Bacillus subtilis
<220> FEATURE:
<221> NAME/KEY: CDS
<222> LOCATION: (1)..(816)

<400> SEQUENCE: 53 ttg aag gac aga att gaa cgc gca gcc gct ttt att aaa caa aac ctg      48
Met Lys Asp Arg Ile Glu Arg Ala Ala Ala Phe Ile Lys Gln Asn Leu
1               5                   10                  15 ccg gaa tct cca aag atc ggc ctt att tta ggc tca ggt ctt ggc att      96
Pro Glu Ser Pro Lys Ile Gly Leu Ile Leu Gly Ser Gly Leu Gly Ile
            20                  25                  30 ttg gcg gac gaa atc gaa aat ccg gtc aag ctg aaa tat gaa gat ata     144
Leu Ala Asp Glu Ile Glu Asn Pro Val Lys Leu Lys Tyr Glu Asp Ile
        35                  40                  45 cct gaa ttc ccg gta tct act gtt gaa ggg cat gcc gga cag ctt gtg     192
Pro Glu Phe Pro Val Ser Thr Val Glu Gly His Ala Gly Gln Leu Val
    50                  55                  60 ctt ggc act ctt gaa gga gtt tcc gtc att gca atg cag ggc cgc ttt     240
Leu Gly Thr Leu Glu Gly Val Ser Val Ile Ala Met Gln Gly Arg Phe
65                  70                  75                  80
```

```
cat ttt tat gaa ggc tac tca atg gag aaa gtc aca ttc cct gta cgc      288
His Phe Tyr Glu Gly Tyr Ser Met Glu Lys Val Thr Phe Pro Val Arg
                85                  90                  95 gtg atg aaa gcg ctc ggt gtg gaa gcg ttg atc gtg aca aat gcc gca      336
Val Met Lys Ala Leu Gly Val Glu Ala Leu Ile Val Thr Asn Ala Ala
            100                 105                 110 ggc ggt gtc aac act gaa ttc cgt gcg gga gat tta atg att att acc      384
Gly Gly Val Asn Thr Glu Phe Arg Ala Gly Asp Leu Met Ile Ile Thr
            115                 120                 125 gat cat atc aac ttt atg gga aca aac ccg tta atc ggg cca aac gaa      432
Asp His Ile Asn Phe Met Gly Thr Asn Pro Leu Ile Gly Pro Asn Glu
130                 135                 140 gca gat ttc ggc gcc aga ttt cca gat atg tct tca gcc tat gac aaa      480
Ala Asp Phe Gly Ala Arg Phe Pro Asp Met Ser Ser Ala Tyr Asp Lys
145                 150                 155                 160 gat ctg tcc agc ctg gct gaa aag att gcg aaa gac ctt aat atc cca      528
Asp Leu Ser Ser Leu Ala Glu Lys Ile Ala Lys Asp Leu Asn Ile Pro
                165                 170                 175 att caa aaa ggc gtg tac act gct gtg aca gga cct tct tac gaa aca      576
Ile Gln Lys Gly Val Tyr Thr Ala Val Thr Gly Pro Ser Tyr Glu Thr
            180                 185                 190 ccg gca gaa gtc cgt ttc tta aga acg atg ggc tct gat gca gtc ggc      624
Pro Ala Glu Val Arg Phe Leu Arg Thr Met Gly Ser Asp Ala Val Gly
            195                 200                 205 atg tct act gtt ccg gaa gtc att gta gcg aat cat gcg gga atg cgg      672
Met Ser Thr Val Pro Glu Val Ile Val Ala Asn His Ala Gly Met Arg
            210                 215                 220 gtt ctt ggc att tcc tgc atc tct aac gcg gca gcc gga att ctg gat      720
Val Leu Gly Ile Ser Cys Ile Ser Asn Ala Ala Ala Gly Ile Leu Asp
225                 230                 235                 240 cag cct tta agt cac gat gaa gtt atg gaa gtg acc gaa aaa gta aaa      768
Gln Pro Leu Ser His Asp Glu Val Met Glu Val Thr Glu Lys Val Lys
                245                 250                 255 gct gga ttc tta aag ctt gtt aaa gcg atc gtc gct cag tac gaa taa      816
Ala Gly Phe Leu Lys Leu Val Lys Ala Ile Val Ala Gln Tyr Glu
            260                 265                 270

<210> SEQ ID NO 54
<211> LENGTH: 271
<212> TYPE: PRT
<213> ORGANISM: Bacillus subtilis

<400> SEQUENCE: 54

Met Lys Asp Arg Ile Glu Arg Ala Ala Ala Phe Ile Lys Gln Asn Leu
1               5                   10                  15

Pro Glu Ser Pro Lys Ile Gly Leu Ile Leu Gly Ser Gly Leu Gly Ile
                20                  25                  30

Leu Ala Asp Glu Ile Glu Asn Pro Val Lys Leu Lys Tyr Glu Asp Ile
            35                  40                  45

Pro Glu Phe Pro Val Ser Thr Val Glu Gly His Ala Gly Gln Leu Val
        50                  55                  60

Leu Gly Thr Leu Glu Gly Val Ser Val Ile Ala Met Gln Gly Arg Phe
65                  70                  75                  80

His Phe Tyr Glu Gly Tyr Ser Met Glu Lys Val Thr Phe Pro Val Arg
                85                  90                  95

Val Met Lys Ala Leu Gly Val Glu Ala Leu Ile Val Thr Asn Ala Ala
            100                 105                 110

Gly Gly Val Asn Thr Glu Phe Arg Ala Gly Asp Leu Met Ile Ile Thr
```

```
                115                 120                 125
Asp His Ile Asn Phe Met Gly Thr Asn Pro Leu Ile Gly Pro Asn Glu
    130                 135                 140

Ala Asp Phe Gly Ala Arg Phe Pro Asp Met Ser Ser Ala Tyr Asp Lys
145                 150                 155                 160

Asp Leu Ser Ser Leu Ala Glu Lys Ile Ala Lys Asp Leu Asn Ile Pro
                165                 170                 175

Ile Gln Lys Gly Val Tyr Thr Ala Val Thr Gly Pro Ser Tyr Glu Thr
            180                 185                 190

Pro Ala Glu Val Arg Phe Leu Arg Thr Met Gly Ser Asp Ala Val Gly
        195                 200                 205

Met Ser Thr Val Pro Glu Val Ile Val Ala Asn His Ala Gly Met Arg
    210                 215                 220

Val Leu Gly Ile Ser Cys Ile Ser Asn Ala Ala Gly Ile Leu Asp
225                 230                 235                 240

Gln Pro Leu Ser His Asp Glu Val Met Glu Val Thr Glu Lys Val Lys
                245                 250                 255

Ala Gly Phe Leu Lys Leu Val Lys Ala Ile Val Ala Gln Tyr Glu
            260                 265                 270

<210> SEQ ID NO 55
<211> LENGTH: 702
<212> TYPE: DNA
<213> ORGANISM: Bacillus subtilis
<220> FEATURE:
<221> NAME/KEY: CDS
<222> LOCATION: (1)..(702)

<400> SEQUENCE: 55 atg agt gta cat ata ggt gct gaa aaa gga caa att gcg gat act gtg        48
Met Ser Val His Ile Gly Ala Glu Lys Gly Gln Ile Ala Asp Thr Val
1               5                   10                  15 ctt ttg ccg gga gat cct ctc aga gca aaa ttt att gca gaa acg tat       96
Leu Leu Pro Gly Asp Pro Leu Arg Ala Lys Phe Ile Ala Glu Thr Tyr
                20                  25                  30 ctt gaa aat gta gaa tgc tac aat gaa gtc aga ggc atg tat gga ttt      144
Leu Glu Asn Val Glu Cys Tyr Asn Glu Val Arg Gly Met Tyr Gly Phe
            35                  40                  45 acg ggt aca tat aaa ggt aaa aaa atc tca gta caa ggc acg gga atg      192
Thr Gly Thr Tyr Lys Gly Lys Lys Ile Ser Val Gln Gly Thr Gly Met
        50                  55                  60 gga gtt ccg tct att tca att tat gtg aat gaa tta att caa agc tac      240
Gly Val Pro Ser Ile Ser Ile Tyr Val Asn Glu Leu Ile Gln Ser Tyr
65                  70                  75                  80 gat gtg caa aat cta ata aga gtc ggt tcc tgc ggc gct att cgt aaa      288
Asp Val Gln Asn Leu Ile Arg Val Gly Ser Cys Gly Ala Ile Arg Lys
                85                  90                  95 gat gtc aaa gtg cga gac gtc att ttg gcg atg acc tcc tca act gat      336
Asp Val Lys Val Arg Asp Val Ile Leu Ala Met Thr Ser Ser Thr Asp
            100                 105                 110 tca caa atg aac aga gtt gct ttc gga agc gtt gat ttt gcg cct tgc      384
Ser Gln Met Asn Arg Val Ala Phe Gly Ser Val Asp Phe Ala Pro Cys
        115                 120                 125 gca gat ttc gag ctt tta aaa aat gcc tat gat gcc gca aag gat aaa      432
Ala Asp Phe Glu Leu Leu Lys Asn Ala Tyr Asp Ala Ala Lys Asp Lys
    130                 135                 140 ggt gtg ccg gtg act gta gga agc gta ttt aca gct gac cag ttc tac      480
Gly Val Pro Val Thr Val Gly Ser Val Phe Thr Ala Asp Gln Phe Tyr
145                 150                 155                 160
```

```
aat gac gat tcg caa att gaa aaa ctt gca aaa tac ggt gtg ctt ggc    528
Asn Asp Asp Ser Gln Ile Glu Lys Leu Ala Lys Tyr Gly Val Leu Gly
                165                 170                 175 gtt gaa atg gaa aca act gca ttg tat aca tta gca gcg aag cac gga    576
Val Glu Met Glu Thr Thr Ala Leu Tyr Thr Leu Ala Ala Lys His Gly
    180                 185                 190 aga aaa gcc ctg tca att ctc acc gtg agt gat cac gta tta aca gga    624
Arg Lys Ala Leu Ser Ile Leu Thr Val Ser Asp His Val Leu Thr Gly
            195                 200                 205 gaa gaa acg aca gcg gaa gag cgt caa acg aca ttt cat gat atg ata    672
Glu Glu Thr Thr Ala Glu Glu Arg Gln Thr Thr Phe His Asp Met Ile
210                 215                 220 gaa gtg gct tta cat tcc gta tca caa taa                            702
Glu Val Ala Leu His Ser Val Ser Gln
225                 230

<210> SEQ ID NO 56
<211> LENGTH: 233
<212> TYPE: PRT
<213> ORGANISM: Bacillus subtilis

<400> SEQUENCE: 56

Met Ser Val His Ile Gly Ala Glu Lys Gly Gln Ile Ala Asp Thr Val
1               5                   10                  15

Leu Leu Pro Gly Asp Pro Leu Arg Ala Lys Phe Ile Ala Glu Thr Tyr
            20                  25                  30

Leu Glu Asn Val Glu Cys Tyr Asn Glu Val Arg Gly Met Tyr Gly Phe
        35                  40                  45

Thr Gly Thr Tyr Lys Gly Lys Lys Ile Ser Val Gln Gly Thr Gly Met
    50                  55                  60

Gly Val Pro Ser Ile Ser Ile Tyr Val Asn Glu Leu Ile Gln Ser Tyr
65                  70                  75                  80

Asp Val Gln Asn Leu Ile Arg Val Gly Ser Cys Gly Ala Ile Arg Lys
                85                  90                  95

Asp Val Lys Val Arg Asp Val Ile Leu Ala Met Thr Ser Ser Thr Asp
            100                 105                 110

Ser Gln Met Asn Arg Val Ala Phe Gly Ser Val Asp Phe Ala Pro Cys
        115                 120                 125

Ala Asp Phe Glu Leu Leu Lys Asn Ala Tyr Asp Ala Ala Lys Asp Lys
    130                 135                 140

Gly Val Pro Val Thr Val Gly Ser Val Phe Thr Ala Asp Gln Phe Tyr
145                 150                 155                 160

Asn Asp Asp Ser Gln Ile Glu Lys Leu Ala Lys Tyr Gly Val Leu Gly
                165                 170                 175

Val Glu Met Glu Thr Thr Ala Leu Tyr Thr Leu Ala Ala Lys His Gly
            180                 185                 190

Arg Lys Ala Leu Ser Ile Leu Thr Val Ser Asp His Val Leu Thr Gly
        195                 200                 205

Glu Glu Thr Thr Ala Glu Glu Arg Gln Thr Thr Phe His Asp Met Ile
    210                 215                 220

Glu Val Ala Leu His Ser Val Ser Gln
225                 230

<210> SEQ ID NO 57
<211> LENGTH: 954
<212> TYPE: DNA
<213> ORGANISM: Bacillus subtilis
```

```
-continued

<220> FEATURE:
<221> NAME/KEY: CDS
<222> LOCATION: (1)..(954)

<400> SEQUENCE: 57 atg tct aat caa tac gga gat aag aat tta aag att ttt tct ttg aat        48
Met Ser Asn Gln Tyr Gly Asp Lys Asn Leu Lys Ile Phe Ser Leu Asn
1               5                   10                  15 tcg aat cca gag ctt gca aaa gaa atc gca gat ata gtt gga gtt caa        96
Ser Asn Pro Glu Leu Ala Lys Glu Ile Ala Asp Ile Val Gly Val Gln
            20                  25                  30 tta ggg aaa tgt tct gtc aca aga ttt agt gac ggg gaa gtc caa att       144
Leu Gly Lys Cys Ser Val Thr Arg Phe Ser Asp Gly Glu Val Gln Ile
        35                  40                  45 aat atc gaa gaa agt att cgc gga tgt gat tgt tac atc atc cag tct       192
Asn Ile Glu Glu Ser Ile Arg Gly Cys Asp Cys Tyr Ile Ile Gln Ser
    50                  55                  60 aca agt gac ccc gtt aac gag cat att atg gaa ctg ctg att atg gta       240
Thr Ser Asp Pro Val Asn Glu His Ile Met Glu Leu Leu Ile Met Val
65                  70                  75                  80 gat gcg tta aaa cgc gct tct gca aaa acg att aac att gtt att cct       288
Asp Ala Leu Lys Arg Ala Ser Ala Lys Thr Ile Asn Ile Val Ile Pro
                85                  90                  95 tat tac ggt tat gcg cgt caa gac aga aaa gca aga tcc cgt gag cca       336
Tyr Tyr Gly Tyr Ala Arg Gln Asp Arg Lys Ala Arg Ser Arg Glu Pro
            100                 105                 110 atc aca gct aaa ctt ttc gct aac ctg ctt gaa aca gcc ggt gcg act       384
Ile Thr Ala Lys Leu Phe Ala Asn Leu Leu Glu Thr Ala Gly Ala Thr
        115                 120                 125 cgt gtg att gca ctt gac ctg cat gcg ccg caa att caa gga ttc ttt       432
Arg Val Ile Ala Leu Asp Leu His Ala Pro Gln Ile Gln Gly Phe Phe
    130                 135                 140 gat ata ccg att gac cac tta atg ggt gtt ccg att tta gga gaa tat       480
Asp Ile Pro Ile Asp His Leu Met Gly Val Pro Ile Leu Gly Glu Tyr
145                 150                 155                 160 ttt gaa ggc aaa aat ctt gaa gat atc gtc att gtt tca cca gac cat       528
Phe Glu Gly Lys Asn Leu Glu Asp Ile Val Ile Val Ser Pro Asp His
                165                 170                 175 ggc ggt gtg aca cgt gcc cgc aaa ctg gct gac cga cta aaa gcg cca       576
Gly Gly Val Thr Arg Ala Arg Lys Leu Ala Asp Arg Leu Lys Ala Pro
            180                 185                 190 att gcg att atc gat aaa cgc cgt ccg cgt cca aac gtg gcg gaa gtc       624
Ile Ala Ile Ile Asp Lys Arg Arg Pro Arg Pro Asn Val Ala Glu Val
        195                 200                 205 atg aat att gta ggt aac atc gaa ggg aag act gct atc ctc atc gat       672
Met Asn Ile Val Gly Asn Ile Glu Gly Lys Thr Ala Ile Leu Ile Asp
    210                 215                 220 gac att att gat act gca ggt acg att aca ctt gct gct aat gcg ctc       720
Asp Ile Ile Asp Thr Ala Gly Thr Ile Thr Leu Ala Ala Asn Ala Leu
225                 230                 235                 240 gtt gaa aac gga gcg aaa gaa gta tat gca tgc tgt aca cac cct gta       768
Val Glu Asn Gly Ala Lys Glu Val Tyr Ala Cys Cys Thr His Pro Val
                245                 250                 255 cta tca ggc cct gcg gtt gaa cgg att aat aat tca aca att aaa gag       816
Leu Ser Gly Pro Ala Val Glu Arg Ile Asn Asn Ser Thr Ile Lys Glu
            260                 265                 270 ctt gtt gtg aca aac agc atc aag ctt cct gaa gaa aag aaa att gaa       864
Leu Val Val Thr Asn Ser Ile Lys Leu Pro Glu Glu Lys Lys Ile Glu
        275                 280                 285 cgc ttt aag cag ctt tca gtc gga ccg ctt ctg gcc gaa gcg att att       912
Arg Phe Lys Gln Leu Ser Val Gly Pro Leu Leu Ala Glu Ala Ile Ile
```

```
Arg Phe Lys Gln Leu Ser Val Gly Pro Leu Leu Ala Glu Ala Ile Ile
    290                 295                 300 cgc gtt cat gag cag caa tca gtc agc tat ctg ttc agc taa                954
Arg Val His Glu Gln Gln Ser Val Ser Tyr Leu Phe Ser
305                 310                 315

<210> SEQ ID NO 58
<211> LENGTH: 317
<212> TYPE: PRT
<213> ORGANISM: Bacillus subtilis

<400> SEQUENCE: 58

Met Ser Asn Gln Tyr Gly Asp Lys Asn Leu Lys Ile Phe Ser Leu Asn
1               5                   10                  15

Ser Asn Pro Glu Leu Ala Lys Glu Ile Ala Asp Ile Val Gly Val Gln
                20                  25                  30

Leu Gly Lys Cys Ser Val Thr Arg Phe Ser Asp Gly Glu Val Gln Ile
            35                  40                  45

Asn Ile Glu Glu Ser Ile Arg Gly Cys Asp Cys Tyr Ile Ile Gln Ser
        50                  55                  60

Thr Ser Asp Pro Val Asn Glu His Ile Met Glu Leu Leu Ile Met Val
65                  70                  75                  80

Asp Ala Leu Lys Arg Ala Ser Ala Lys Thr Ile Asn Ile Val Ile Pro
                85                  90                  95

Tyr Tyr Gly Tyr Ala Arg Gln Asp Arg Lys Ala Arg Ser Arg Glu Pro
            100                 105                 110

Ile Thr Ala Lys Leu Phe Ala Asn Leu Leu Glu Thr Ala Gly Ala Thr
        115                 120                 125

Arg Val Ile Ala Leu Asp Leu His Ala Pro Gln Ile Gln Gly Phe Phe
130                 135                 140

Asp Ile Pro Ile Asp His Leu Met Gly Val Pro Ile Leu Gly Glu Tyr
145                 150                 155                 160

Phe Glu Gly Lys Asn Leu Glu Asp Ile Val Ile Val Ser Pro Asp His
                165                 170                 175

Gly Gly Val Thr Arg Ala Arg Lys Leu Ala Asp Arg Leu Lys Ala Pro
            180                 185                 190

Ile Ala Ile Ile Asp Lys Arg Arg Pro Arg Pro Asn Val Ala Glu Val
        195                 200                 205

Met Asn Ile Val Gly Asn Ile Glu Gly Lys Thr Ala Ile Leu Ile Asp
210                 215                 220

Asp Ile Ile Asp Thr Ala Gly Thr Ile Thr Leu Ala Ala Asn Ala Leu
225                 230                 235                 240

Val Glu Asn Gly Ala Lys Glu Val Tyr Ala Cys Cys Thr His Pro Val
                245                 250                 255

Leu Ser Gly Pro Ala Val Glu Arg Ile Asn Asn Ser Thr Ile Lys Glu
            260                 265                 270

Leu Val Val Thr Asn Ser Ile Lys Leu Pro Glu Glu Lys Lys Ile Glu
        275                 280                 285

Arg Phe Lys Gln Leu Ser Val Gly Pro Leu Leu Glu Ala Ile Ile
290                 295                 300

Arg Val His Glu Gln Gln Ser Val Ser Tyr Leu Phe Ser
305                 310                 315

<210> SEQ ID NO 59
<211> LENGTH: 17
<212> TYPE: DNA
```

<210> SEQ ID NO 59
<211> LENGTH: 17
<212> TYPE: DNA
<213> ORGANISM: Artificial sequence
<220> FEATURE:
<223> OTHER INFORMATION: primer

<400> SEQUENCE: 59
gaagttgatg atcaaaa                                                17

<210> SEQ ID NO 60
<211> LENGTH: 19
<212> TYPE: DNA
<213> ORGANISM: Artificial sequence
<220> FEATURE:
<223> OTHER INFORMATION: primer

<400> SEQUENCE: 60
acatattgtt gacgataat                                              19

<210> SEQ ID NO 61
<211> LENGTH: 1467
<212> TYPE: DNA
<213> ORGANISM: Bacillus subtilis
<220> FEATURE:
<221> NAME/KEY: CDS
<222> LOCATION: (1)..(1464)

<400> SEQUENCE: 61

```
atg tgg gaa agt aaa ttt tca aaa gaa ggc tta acg ttc gac gat gtg      48
Met Trp Glu Ser Lys Phe Ser Lys Glu Gly Leu Thr Phe Asp Asp Val
1               5                   10                  15 ctt gta cca gca aag tct gag gta ctt ccg cgt gat gtg gat tta          96
Leu Val Pro Ala Lys Ser Glu Val Leu Pro Arg Asp Val Asp Leu
            20                  25                  30 tct gta gaa ctt aca aaa acg tta aag cta aat att cct gtc atc agc     144
Ser Val Glu Leu Thr Lys Thr Leu Lys Leu Asn Ile Pro Val Ile Ser
35                  40                  45 gca ggt atg gac act gta aca gaa tca gca atg gca att gca atg gca     192
Ala Gly Met Asp Thr Val Thr Glu Ser Ala Met Ala Ile Ala Met Ala
    50                  55                  60 aga cag ggc ggc ttg ggc atc att cac aaa aat atg tcc att gaa cag     240
Arg Gln Gly Gly Leu Gly Ile Ile His Lys Asn Met Ser Ile Glu Gln
65                  70                  75                  80 cag gct gaa caa gtt gat aaa gta aag cgt tct gag cgc ggc gtt atc     288
Gln Ala Glu Gln Val Asp Lys Val Lys Arg Ser Glu Arg Gly Val Ile
                85                  90                  95 aca aat ccc ttc ttt tta act cct gat cac caa gta ttt gat gcg gag     336
Thr Asn Pro Phe Phe Leu Thr Pro Asp His Gln Val Phe Asp Ala Glu
            100                 105                 110 cat ttg atg ggg aaa tac aga att tcc ggt gtt ccg att gta aat aac     384
His Leu Met Gly Lys Tyr Arg Ile Ser Gly Val Pro Ile Val Asn Asn
        115                 120                 125 gaa gaa gac cag aag ctt gtt gga att att aca aac cgt gac ctt cgt     432
Glu Glu Asp Gln Lys Leu Val Gly Ile Ile Thr Asn Arg Asp Leu Arg
    130                 135                 140 ttt att tct gac tac tca atg aaa atc agc gac gtc atg acg aaa gaa     480
Phe Ile Ser Asp Tyr Ser Met Lys Ile Ser Asp Val Met Thr Lys Glu
145                 150                 155                 160 gag cta gtt act gca tct gta gga act act ctg gat gaa gct gaa aag     528
Glu Leu Val Thr Ala Ser Val Gly Thr Thr Leu Asp Glu Ala Glu Lys
                165                 170                 175 att ttg cag aaa cat aaa att gaa aag ctt cct ctc gta gat gac cag     576
Ile Leu Gln Lys His Lys Ile Glu Lys Leu Pro Leu Val Asp Asp Gln
            180                 185                 190
```

-continued

```
aat aaa tta aaa ggt ctt atc aca att aaa gac att gaa aaa gtc att      624
Asn Lys Leu Lys Gly Leu Ile Thr Ile Lys Asp Ile Glu Lys Val Ile
        195                 200                 205 gag ttc ccg aac tca tct aaa gac att cac ggc cgc ctg atc gtt ggc      672
Glu Phe Pro Asn Ser Ser Lys Asp Ile His Gly Arg Leu Ile Val Gly
210                 215                 220 gcg gca gtt ggt gta act ggc gat aca atg act cgc gtc aaa aag ctt      720
Ala Ala Val Gly Val Thr Gly Asp Thr Met Thr Arg Val Lys Lys Leu
225                 230                 235                 240 gtt gaa gcc aat gtt gat gtg att gtt atc gat aca gct cac gga cac      768
Val Glu Ala Asn Val Asp Val Ile Val Ile Asp Thr Ala His Gly His
                245                 250                 255 tct caa ggc gtt tta aac aca gtc aca aaa atc cgt gaa acg tat ccc      816
Ser Gln Gly Val Leu Asn Thr Val Thr Lys Ile Arg Glu Thr Tyr Pro
            260                 265                 270 gaa tta aac att att gct gga aac gtg gca aca gct gaa gcg aca aga      864
Glu Leu Asn Ile Ile Ala Gly Asn Val Ala Thr Ala Glu Ala Thr Arg
        275                 280                 285 gcg ctt atc gaa gct gga gca gac gtt gtc aaa gtt gga ata ggg cct      912
Ala Leu Ile Glu Ala Gly Ala Asp Val Val Lys Val Gly Ile Gly Pro
290                 295                 300 ggt tca att tgt act aca cgt gtt gta gcc ggc gtg ggt gtt ccg caa      960
Gly Ser Ile Cys Thr Thr Arg Val Val Ala Gly Val Gly Val Pro Gln
305                 310                 315                 320 att aca gca att tat gat tgt gcg act gaa gca aga aaa cac ggc aaa     1008
Ile Thr Ala Ile Tyr Asp Cys Ala Thr Glu Ala Arg Lys His Gly Lys
                325                 330                 335 aca atc atc gcc gac ggt ggg att aaa ttc tct ggc gat atc act aaa     1056
Thr Ile Ile Ala Asp Gly Gly Ile Lys Phe Ser Gly Asp Ile Thr Lys
            340                 345                 350 gca ttg gca gcc ggc gga cat gct gtt atg ctc gga agc ttg ctt gca     1104
Ala Leu Ala Ala Gly Gly His Ala Val Met Leu Gly Ser Leu Leu Ala
        355                 360                 365 ggc aca tca gaa agc cct ggt gaa act gaa atc tac caa ggc aga aga     1152
Gly Thr Ser Glu Ser Pro Gly Glu Thr Glu Ile Tyr Gln Gly Arg Arg
370                 375                 380 ttt aag gta tac cgc ggc atg gga tca gtt gct gca atg gaa aaa gga     1200
Phe Lys Val Tyr Arg Gly Met Gly Ser Val Ala Ala Met Glu Lys Gly
385                 390                 395                 400 agt aaa gac cgt tac ttc caa gaa gaa aac aaa aaa ttt gtt cct gaa     1248
Ser Lys Asp Arg Tyr Phe Gln Glu Glu Asn Lys Lys Phe Val Pro Glu
                405                 410                 415 gga att gaa gga cgc aca cct tac aaa ggg cca gtt gaa gaa acc gtt     1296
Gly Ile Glu Gly Arg Thr Pro Tyr Lys Gly Pro Val Glu Glu Thr Val
            420                 425                 430 tat cag cta gtc gga ggc ctt cgt tct ggt atg ggg tat tgc ggg tcc     1344
Tyr Gln Leu Val Gly Gly Leu Arg Ser Gly Met Gly Tyr Cys Gly Ser
        435                 440                 445 aaa gat ctg cgt gcg cta aga gaa gaa gct cag ttc att cgc atg act     1392
Lys Asp Leu Arg Ala Leu Arg Glu Glu Ala Gln Phe Ile Arg Met Thr
450                 455                 460 ggc gca gga ctt cgc gaa agc cat ccg cat gac gta cag att aca aaa     1440
Gly Ala Gly Leu Arg Glu Ser His Pro His Asp Val Gln Ile Thr Lys
465                 470                 475                 480 gaa tca cct aac tat aca att tca taa                                 1467
Glu Ser Pro Asn Tyr Thr Ile Ser
                485
```

<210> SEQ ID NO 62
<211> LENGTH: 488

<212> TYPE: PRT
<213> ORGANISM: Bacillus subtilis

<400> SEQUENCE: 62

```
Met Trp Glu Ser Lys Phe Ser Lys Glu Gly Leu Thr Phe Asp Asp Val
1               5                   10                  15

Leu Leu Val Pro Ala Lys Ser Glu Val Leu Pro Arg Asp Val Asp Leu
            20                  25                  30

Ser Val Glu Leu Thr Lys Thr Leu Lys Leu Asn Ile Pro Val Ile Ser
        35                  40                  45

Ala Gly Met Asp Thr Val Thr Glu Ser Ala Met Ala Ile Ala Met Ala
    50                  55                  60

Arg Gln Gly Gly Leu Gly Ile Ile His Lys Asn Met Ser Ile Glu Gln
65                  70                  75                  80

Gln Ala Glu Gln Val Asp Lys Val Lys Arg Ser Glu Arg Gly Val Ile
                85                  90                  95

Thr Asn Pro Phe Phe Leu Thr Pro Asp His Gln Val Phe Asp Ala Glu
            100                 105                 110

His Leu Met Gly Lys Tyr Arg Ile Ser Gly Val Pro Ile Val Asn Asn
        115                 120                 125

Glu Glu Asp Gln Lys Leu Val Gly Ile Ile Thr Asn Arg Asp Leu Arg
    130                 135                 140

Phe Ile Ser Asp Tyr Ser Met Lys Ile Ser Asp Val Met Thr Lys Glu
145                 150                 155                 160

Glu Leu Val Thr Ala Ser Val Gly Thr Thr Leu Asp Glu Ala Glu Lys
                165                 170                 175

Ile Leu Gln Lys His Lys Ile Glu Lys Leu Pro Leu Val Asp Asp Gln
            180                 185                 190

Asn Lys Leu Lys Gly Leu Ile Thr Ile Lys Asp Ile Glu Lys Val Ile
        195                 200                 205

Glu Phe Pro Asn Ser Ser Lys Asp Ile His Gly Arg Leu Ile Val Gly
    210                 215                 220

Ala Ala Val Gly Val Thr Gly Asp Thr Met Thr Arg Val Lys Lys Leu
225                 230                 235                 240

Val Glu Ala Asn Val Asp Val Ile Val Ile Asp Thr Ala His Gly His
                245                 250                 255

Ser Gln Gly Val Leu Asn Thr Val Thr Lys Ile Arg Glu Thr Tyr Pro
            260                 265                 270

Glu Leu Asn Ile Ile Ala Gly Asn Val Ala Thr Ala Glu Ala Thr Arg
        275                 280                 285

Ala Leu Ile Glu Ala Gly Ala Asp Val Val Lys Val Gly Ile Gly Pro
    290                 295                 300

Gly Ser Ile Cys Thr Thr Arg Val Val Ala Gly Val Gly Val Pro Gln
305                 310                 315                 320

Ile Thr Ala Ile Tyr Asp Cys Ala Thr Glu Ala Arg Lys His Gly Lys
                325                 330                 335

Thr Ile Ile Ala Asp Gly Gly Ile Lys Phe Ser Gly Asp Ile Thr Lys
            340                 345                 350

Ala Leu Ala Ala Gly Gly His Ala Val Met Leu Gly Ser Leu Leu Ala
        355                 360                 365

Gly Thr Ser Glu Ser Pro Gly Glu Thr Glu Ile Tyr Gln Gly Arg Arg
    370                 375                 380

Phe Lys Val Tyr Arg Gly Met Gly Ser Val Ala Ala Met Glu Lys Gly
385                 390                 395                 400
```

```
Ser Lys Asp Arg Tyr Phe Gln Glu Glu Asn Lys Lys Phe Val Pro Glu
            405                 410                 415

Gly Ile Glu Gly Arg Thr Pro Tyr Lys Gly Pro Val Glu Glu Thr Val
            420                 425                 430

Tyr Gln Leu Val Gly Gly Leu Arg Ser Gly Met Gly Tyr Cys Gly Ser
        435                 440                 445

Lys Asp Leu Arg Ala Leu Arg Glu Glu Ala Gln Phe Ile Arg Met Thr
        450                 455                 460

Gly Ala Gly Leu Arg Glu Ser His Pro His Asp Val Gln Ile Thr Lys
465                 470                 475                 480

Glu Ser Pro Asn Tyr Thr Ile Ser
                485
```

PURINE-DERIVED SUBSTANCE-PRODUCING BACTERIUM AND A METHOD FOR PRODUCING PURINE-DERIVED SUBSTANCE

The present application claims priority under 35 U.S.C. § 119(a) to Japanese Patent Application Nos. 2005-067560, filed Mar. 10, 2005, and 2005-280186, filed Sep. 27, 2006, the entireties of which are incorporated by reference. Also, the Sequence Listing on compact disk filed herewith is hereby incorporated by reference (File name: US-271 Seq List; File size: 59 KB; Date recorded: Mar. 9, 2006).

BACKGROUND OF THE INVENTION

1. Field of the Invention

The present invention relates to a *Bacillus* bacterium which is useful for the production of purine-derived substances, including purine nucleotides such as 5'-inosinic acid and 5'-guanylic acid, and purine nucleosides such as inosine and guanosine. These nucleosides are important as starting materials for making purine nucleotides. Purine-derived substances are useful as seasonings, pharmaceuticals, and raw materials thereof.

2. Brief Description of the Related Art

Methods for producing inosine and guanosine by fermentation using adenine-auxotrophic mutants of *Bacillus* bacteria and derivatives thereof which are imparted with resistance to various drugs such as purine analogs (JP38-23099B, JP54-17033B, JP55-2956B, JP55-45199B, JP57-14160B, JP57-41915B, JP59-42895A, and US2004-0166575 A) have been previously described. Also, methods using mutants of *Brevibacterium* bacteria (JP51-5075B, JP58-17592B and Agric. Biol. Chem., 1978, 42, 399-405) have been described.

Such mutants are typically obtained by treating the cells with UV irradiation or N-methyl-N'-nitro-N-nitrosoguanidine, and selecting a target mutant in a suitable selective medium.

Strains which produce purine-derived substances have also been bred using genetic engineering techniques in *Bacillus* bacteria (JP58-158197A, JP58-175493A, JP59-28470A, JP60-156388A, JP1-27477A, JP1-174385A, JP3-58787A, JP3-164185A, JP5-84067A, and JP5-192164A), *Brevibacterium* bacteria (JP63-248394A), and *Escherichia* bacteria (WO99/03988). Specifically, a method of efficiently producing nucleic acid-derived substances such as hypoxanthine, uracil, guanine, and adenine with a *Bacillus* bacterium in which a gene (purR gene) encoding the purine operon repressor is disrupted is disclosed in U.S. Pat. No. 6,284,495.

In *Bacillus subtilis*, the purine operon repressor is known to regulate the expression of the purA. This gene is involved in AMP biosynthesis (Proc. Natl. Acad. Sci, USA, 1995, 92, 7455-7459). This repressor also regulates the expression of the glyA gene, which is involved formyltetrahydrofolate biosynthesis (J. Bacteriol., 2001, 183, 6175-6183), and the pbuG gene which encodes a hypoxanthine/guanine transporter (J. Bacteriol., 2003, 185, 5200-5209.), in addition to the purine operon gene.

A method for breeding a strain which efficiently produces inosine by disrupting the succinyl-AMP-synthase gene (purA) to impart adenine-auxotrophy and disrupting the purine nucleoside phosphorylase gene (deoD) to inhibit the decomposition of inosine into hypoxanthine in addition to disrupting the purR gene is described in US2004-0166575 A.

Meanwhile, in the oxidative pentosephosphate pathway, glucose is phosphorylated by glucose kinase to generate glucose-6-phosphate, which is oxidatively converted to ribose-5-phosphate. However, the relationship between this pathway and the biosynthetic pathway of purine-derived substances is not well understood; and therefore, it was not expected that a bacterium which produces purine-derived substances could be obtained by modifying the oxidative pentosephosphate pathway of the bacterium.

SUMMARY OF THE INVENTION

The object of the present invention is to provide a bacterium suitable for producing purine-derived substances such as purine nucleosides and purine nucleotides by fermentation, and to provide a method for producing purine-derived substances using such a bacterium.

The inventors of the present invention conducted extensive studies for solving the above-mentioned object, and found that the ability to produce purine-derived substances such as purine nucleosides and purine nucleotides of a *Bacillus* bacterium could be enhanced by increasing an activity of an enzyme of the oxidative pentosephosphate pathway, particularly the activity of glucose-6-phosphate dehydrogenase or ribose-5-phosphate isomerase. They also found that the ability to produce a purine-derived substance in a *Bacillus* bacterium could be further enhanced by further modification which results in enhancing the expression of a gene encoding phosphoribosylpyrophosphate (PRPP) synthetase or a gene encoding an enzyme involved in purine nucleotide biosynthesis, or to decrease the activity of purine nucleoside phosphorylase. Based on these findings, the present invention has been completed.

It is an object of the present invention to provide a *Bacillus* bacterium having an ability to produce a purine-derived substance, wherein the bacterium is modified to enhance an activity of an enzyme of the oxidative pentose-phosphate pathway.

It is a further object of the present invention to provide the *Bacillus* bacterium as described above, wherein said purine-derived substance is selected from the group consisting of inosine, xanthosine, guanosine, and adenosine.

It is a further object of the present invention to provide the *Bacillus* bacterium as described above, wherein said purine-derived substance is selected from the group consisting of inosinic acid, xanthylic acid, guanylic acid, and adenylic acid.

It is a further object of the present invention to provide the *Bacillus* bacterium as described above, wherein said enzyme is glucose-6-phosphate-dehydrogenase or ribose-5-phosphate isomerase.

It is a further object of the present invention to provide the *Bacillus* bacterium as described above, wherein said activity of the enzyme is enhanced by increasing the copy number of a gene encoding the enzyme or modifying an expression control sequence of the gene.

It is a further object of the present invention to provide the *Bacillus* bacterium as described above, wherein said enzyme is glucose-6-phosphate dehydrogenase which is selected from the group consisting of:

(A) a protein comprising the amino acid sequence of SEQ ID NO: 48; and (B) a protein comprising the amino acid sequence of SEQ ID NO: 48, wherein one or several amino acids are substituted, deleted, inserted, added, or inverted, and said protein has glucose-6-phosphate dehydrogenase activity.

It is a further object of the present invention to provide the *Bacillus* bacterium as described above, wherein said enzyme is ribose-5-phosphate isomerase which is selected from the group consisting of:

(A) a protein comprising the amino acid sequence of SEQ ID NO: 50; and (B) a protein comprising the amino acid sequence of SEQ ID NO: 50 wherein one or several amino acids are substituted, deleted, inserted, added, or inverted, and said protein has ribose-5-phosphate isomerase activity.

It is a further object of the present invention to provide the *Bacillus* bacterium as described above, wherein 1-20 amino acids are substituted, deleted, inserted, added, or inverted.

It is a further object of the present invention to provide the *Bacillus* bacterium as described above, wherein said enzyme is glucose-6-phosphate dehydrogenase and the gene encoding said enzyme is selected from the group consisting of:

(A) a DNA comprising the nucleotide sequence of SEQ ID NO: 47; and (B) a DNA that is able to hybridize with a nucleotide sequence complementary to the nucleotide sequence of SEQ ID NO: 47, or a probe prepared from the nucleotide sequence under stringent conditions, and encodes a protein having glucose-6-phosphate dehydrogenase activity.

It is a further object of the present invention to provide the *Bacillus* bacterium as described above, wherein said enzyme is ribose-5-phosphate isomerase and the gene encoding said enzyme is selected from the group consisting of:

(A) a DNA comprising the nucleotide sequence of SEQ ID NO: 49; and (B) a DNA that is able to hybridize with a nucleotide sequence complementary to the nucleotide sequence of SEQ ID NO: 49, or a probe prepared from the nucleotide sequence under stringent conditions, and encodes a protein having ribose-5-phosphate isomerase activity.

It is a further object of the present invention to provide the *Bacillus* bacterium as described above, wherein the bacterium is further modified to enhance phosphoribosylpyrophosphate synthetase activity.

It is a further object of the present invention to provide the *Bacillus* bacterium as described above, wherein the bacterium is further modified to enhance the expression of purine operon.

It is a further object of the present invention to provide the *Bacillus* bacterium as described above, wherein the expression of the purine operon is enhanced by disrupting a purR gene that encodes a purine operon repressor or deleting a portion of an attenuator region of the purine operon.

It is a further object of the present invention to provide the *Bacillus* bacterium as described above, wherein the bacterium is further modified to reduce the activity of purine nucleoside phosphorylase.

It is a further object of the present invention to provide a method for producing a purine-derived substance comprising:

culturing the *Bacillus* bacterium as described above in a medium; and collecting said purine-derived substance.

It is a further object of the present invention to provide the method as described above, wherein said purine-derived substance is a purine nucleoside or purine nucleotide.

It is a further object of the present invention to provide the method as described above, wherein said purine-derived substance is selected from the group consisting of inosine, xanthosine, guanosine, and adenosine.

It is a further object of the present invention to provide the method as described above, wherein said purine-derived substance is selected from the group consisting of inosinic acid, xanthylic acid, guanylic acid, and adenylic acid.

It is a further object of the present invention to provide a method for producing a purine nucleotide comprising:

producing a purine nucleoside by the method as described above;

reacting the purine nucleoside with a microorganism which has an ability to produce a nucleoside-5'-phosphate ester, or with an acid phosphatase, in the presence of a phosphate donor selected from the group consisting of phosphoric acid, phenyl phosphate, and carbamyl phosphate to produce purine nucleotide; and collecting the purine nucleotide.

The *Bacillus* bacterium of the present invention can be used to efficiently produce purine-derived substances such as purine nucleosides and purine nucleotides.

BRIEF DESCRIPTION OF THE DRAWINGS

FIG. 1 shows the structure of upstream of the purine operon. The nucleotide sequence enclosed in boxes denotes the purine operon promoter; the overlined sequence denotes an antiterminator dyad, and the underlined sequence denotes a terminator dyad. The sequence which will be deleted (75 bp) is indicated by upper-case letters.

FIG. 2 shows the transcription activity of the modified purine operon promoter.

DETAILED DESCRIPTION OF EXEMPLARY EMBODIMENTS

<1>*Bacillus* Bacterium of the Present Invention (I) Imparting the Ability to Produce a Purine-Derived Substance The *Bacillus* bacterium of the present invention has an ability to produce a purine-derived substance and has been modified to enhance the activity of an enzyme of the oxidative pentosephosphate pathway.

The term "purine-derived substance" means a substance having a purine skeleton, and examples thereof include purine nucleosides and purine nucleotides. Examples of purine nucleosides include inosine, xanthosine, guanosine, and adenosine. Examples of purine nucleotides include 5'-phosphate ester of purine nucleosides, specifically, inosinic acid (inosine 5'-monophosphate, also referred to as "IMP" hereinafter), xanthylic acid (xanthosine 5'-monophosphate, also referred to as "XMP" hereinafter), guanylic acid (guanosine 5'-monophosphate, also referred to as "GMP" hereinafter), and adenylic acid (adenosine 5'-monophosphate, also referred to as "AMP" hereinafter).

The phrase "ability to produce a purine-derived substance" means that the *Bacillus* bacterium of the present invention has an ability to produce and cause accumulation of a purine-derived substance in a medium or in the bacterial cells to such an extent that the substance can be collected from the medium or the bacterial cells when it is cultured in the medium. The *Bacillus* bacterium of the present invention may have an ability to produce two or more purine-derived substances.

The *Bacillus* bacterium of the present invention may originally possess the ability to produce a purine-derived substance, or this ability may be imparted by modifying a *Bacillus* bacterium such as those shown below by a mutagenesis or gene recombination techniques. Furthermore, the *Bacillus* bacterium of the present invention may have the ability imparted by a modification which enhances the activity of an enzyme of the oxidative pentosephosphate synthetic pathway.

Examples of the parent strain which can be used to obtain the *Bacillus* bacterium of the present invention include *Bacillus subtilis, Bacillus amyloliquefaciens*, and *Bacillus pumilus*. Examples of *Bacillus subtilis* include *Bacillus subtilis* 168 Marburg strain (ATCC6051) and *Bacillus subtilis* PY79 strain (Plasmid, 1984, 12, 1-9). Examples of *Bacillus amyloliquefaciens* include *Bacillus amyloliquefaciens* T strain (ATCC 23842) and *Bacillus amyloliquefaciens* N strain (ATCC 23845).

The *Bacillus* bacterium having an ability to produce inosine can be obtained by imparting an adenine-auxotrophy, as well as resistance to a drug such as a purine analog to the *Bacillus* bacterium as described above (JP38-23099B, JP54-17033B, JP55-45199B, JP57-14160B, JP57-41915B, and JP59-42895B, US2004-0166575A). A mutant of *Bacillus* bacterium having such an auxotrophy and drug-resistance can be obtained by treating the bacterium with a mutagenesis agent which is commonly employed to introduce mutations, such as N-methyl-N'-nitro-N-nitrosoguanidine (NTG) and ethane methane sulfonate (EMS).

An example of an inosine-producing strain of *Bacillus* bacterium includes the *Bacillus subtilis* KMBS16 strain. This strain is a derived from *Bacillus subtilis* trpC2 strain (168 Marburg), wherein a purR gene encoding a purine operon repressor, a purA gene encoding succinyl-AMP synthase, and a deoD gene encoding purine nucleoside phosphorylase are disrupted (purR::spc, purA::erm, deoD::kan) (US2004-0166575A). *Bacillus subtilis* AJ3772 strain (FERM P-2555) (JP62-014794A) *Bacillus subtilis* 6-ethoxypurine resistant strain (US2004-0166575A) may also be used.

Examples of a *Bacillus* bacterium which has an ability to produce guanosine include a *Bacillus* bacterium which has enhanced IMP dehydrogenase activity (JP3-58787A) and a *Bacillus* bacterium which is obtained by introducing a vector comprising a gene conferring resistant to a purine analog and decoyinine into an adenine-auxotrophic mutant (JP4-28357A).

Examples of a *Bacillus* bacterium which has an ability to produce a purine nucleotide include inosine-producing strains of *Bacillus subtilis* which have attenuated phosphatase activity (Uchida, K. et al, Agr. Biol. Chem., 1961, 25, 804-805; Fujimoto, M., Uchida, K., Agr. Biol. Chem., 1965, 29, 249-259), and mutant of a *Bacillus* bacterium which has an ability to produce 5'-guanylic acid, imparted with an adenine-auxotrophy, and resistance to decoyinine or methionine sulfoxide (JP56-12438B).

Examples of a method for breeding a *Bacillus* bacterium which has the ability to produce a purine-derived substance include enhancing the activities of enzymes involved in purine biosynthesis, and which are common to the biosynthesis of purine nucleosides and nucleotides. The activity of the enzymes is preferably enhanced to a level greater than that of unmodified strain of *Bacillus* bacterium, such as a wild-type strain of *Bacillus* bacterium. The phrase "activity is enhanced" encompasses when the number of enzyme molecules per cell is increased, and when the relative activity of the enzyme molecule is increased. For example, the activity can be enhanced by increasing the expression of the gene encoding the enzyme.

Examples of an enzyme involved in the biosynthesis of purine include phosphoribosylpyrophosphate (PRPP) amidotransferase and PRPP synthetase.

Some of the catabolites derived from sugar sources such as glucose that flow into the pentosephosphate system are converted to ribose-5-phosphate via ribulose-5-phosphate. PRPP, which is a indispensable precursor in the biosynthesis of purine nucleosides, histidine, and tryptophan, is produced from ribose-5-phosphate. Specifically, the ribose-5-phosphate is converted to PRPP by PRPP synthetase [EC: 2.7.6.1]. Accordingly, modifying a *Bacillus* bacterium to enhance the activity of PRPP synthetase imparts the ability to produce a purine-derived substance to the *Bacillus* bacterium, and the combined enhancement of the PRPP synthetase activity with an activity of an enzyme involved in the pentose-phosphate system is more effective.

The phrase "the activity of PRPP synthetase is enhanced" means that the activity of PRPP synthetase increases as compared to an unmodified strain, such as a wild-type strain or a parent strain. The activity of the PRPP synthetase can be measured by the method of Switzer et al. (Methods Enzymol., 1978, 51, 3-11)) or Roth et al. (Methods Enzymol., 1978, 51, 12-17). A *Bacillus* bacterium in which the activity of the PRPP synthetase is enhanced can be obtained by increasing the expression of a gene encoding the PRPP synthetase in the same manner as described in US2004-0166575A, for example, by using a plasmid or integrating the gene into a chromosome. An example of a gene which encodes the PRPP synthetase includes the prs gene (SEQ ID NO: 57, GenBank Accession No. X16518) derived from a *Bacillus* bacterium; however, any gene encoding a protein having PRPP synthetase activity in a *Bacillus* bacterium, including genes derived from other bacteria and genes derived from plants and animals, can also be used.

When PRPP is produced, some of it is converted to purine nucleosides and purine nucleotides by the enzymes involved in purine biosynthesis. The enzymes involved in purine biosynthesis are encoded by the purine operon, and examples of the purine operon include the purEKB-purC (orf)QLF-purMNH(J)-purD operon gene from *Bacillus subtilis* (Ebbole D J and Zalkin H, J. Biol. Chem., 1987, 262, 17, 8274-87) (also known as purEKBCSQLFMNHD: *Bacillus subtilis* and Its Closest Relatives, Editor in Chief: A. L. Sonenshein, ASM Press, Washington, D.C., 2002) and the genes of the pur regulon from *Escherichia coli* (*Escherichia* and *Salmonella*, Second Edition, Editor in Chief: F. C. Neidhardt, ASM press, Washington D.C., 1996).

Accordingly, enhancing the expression of these genes imparts the ability to produce a purine-derived substance. However, genes of the purine operon used in the present invention are not limited to these genes, and genes derived from other microorganisms and from plants and animals may also be used.

Expression of the genes of the pur operon can be enhanced in a *Bacillus* bacterium by using a plasmid containing the gene or integrating the gene into a chromosome in the same manner as enhancing the gene encoding the enzyme of the oxidative pentosephosphate pathway as described below.

The expression of the purine operon can also be enhanced by replacing a promoter of the purine operon with a stronger one, or by replacing the "−35 region", or "−10 region" of the native promoter with a consensus sequence.

For example, in *Bacillus subtilis* (*B. subtilis* 168 Marburg strain; ATCC6051), the "−35 region" of the purine operon is a consensus sequence (TTGACA), but the "−10 region" is TAAGAT, which differs from the consensus sequence TATAAT (Ebbole, D. J. and H. Zalikn, J. Biol. Chem., 1987, 262, 8274-8287). Accordingly, by changing the "−10 sequence" (TAAGAT) to the similar consensus sequence TATAAT, TATGAT, or TAAAAT, it is possible to enhance the transcription activity of the purine operon. A promoter sequence can be replaced by gene substitution, which is described below.

The expression of the purine operon can also be enhanced by decreasing the expression of a purine operon repressor (U.S. Pat. No. 6,284,495).

To decrease the expression of the purine operon repressor, for example, a *Bacillus* bacterium is treated with a mutagenesis agent commonly used in mutation treatment, such as UV irradiation, NTG, or EMS, and the mutants having reduced expression of the purine operon repressor are selected.

Furthermore, the expression of the repressor may be decreased by performing homologous recombination (Experiments in Molecular Genetics, Cold Spring Harbor Laboratory Press (1972); Matsuyama, S. and Mizushima, S., J. Bacteriol., 1985, 162, 1196-1202), so that a gene encoding a purine operon repressor (purR) on the chromosome (GenBank Accession No. NC_000964, SEQ ID NO: 51) is replaced with a mutant gene in which part of the sequence of the repressor is deleted (hereinafter, this may be referred to as a "disrupted-type gene").

For example, a wild-type gene can be replaced with a disrupted-type gene on the host chromosome in the manner as described below. Hereinafter, the disruption of the purR gene is explained. Other genes such as the purA gene and deoD gene can be similarly disrupted.

In homologous recombination, a plasmid that is not capable of replicating in cells of a *Bacillus* bacterium and which has a nucleotide sequence that is homologous with a sequence on the chromosome is introduced into the bacterial cell, resulting in homologous recombination. The plasmid is then recombined into the chromosome in the first recombination (single-cross-over recombination). Then, a second recombination (double-cross-over recombination) occurs and the plasmid is removed from the chromosome. At this time, in some cases, a disrupted-type gene on the plasmid is integrated into the chromosome and the wild-type gene on the chromosome is removed with the plasmid portion from the chromosome. By selecting such bacterial strains, it is possible to obtain bacterial strains in which the wild-type purR gene on the chromosome has been replaced with the disrupted-type purR gene.

Such techniques are established and include a method of using a linear DNA, a method using a temperature-sensitive plasmid, and the like. Furthermore, the purR gene may be disrupted by using a plasmid in which a drug-resistance marker gene has been inserted into the native purR gene which prohibits replication in the target bacterial cell. That is, in a bacterial cell that has been transformed with this plasmid, the marker gene is incorporated into the chromosomal DNA and imparts drug resistance. Since the marker gene is integrated into the chromosome at a high rate by homologous recombination of the purR gene sequences that sandwiches the marker gene on the plasmid with the wild-type purR gene on the chromosome, a purR gene-disrupted strain can be efficiently selected.

Specifically, the disrupted-type purR gene used in gene disruption can be obtained by digesting a wild-type purR gene with restriction enzymes to delete a certain region of the purR gene, followed by self-ligation of the digested DNA, or inserting another DNA fragment (marker gene etc.) into the wild-type purR gene, or causing replacement, deletion, insertion, addition, or inversion of one or several nucleotides in the coding region or promoter region of the nucleotide sequence of the purR gene by a site-specific mutation method (Kramer, W. and Fritz, H. J., Methods Enzymol., 1987, 154, 350-367) or by recombinant PCR (PCR Technology, Stockton Press (1989)) or by treatment with a chemical agent such as sodium sulfite or hydroxylamine (Shortle, D. and Nathans, D., Proc. Natl. Acad. Sci. USA, 1978, 75, 2170-2174), followed by selection of a strain in which the activity of the purine operon repressor is decreased or eliminated or a strain in which transcription of the purR gene is decreased or eliminated. Of these methods, deleting a certain region of the wild-type purR gene by digestion with restriction enzymes followed by self-ligation and inserting another DNA fragment into the wild-type purR gene are preferable in view of reliability and stability.

The purR gene can be obtained by PCR using oligonucleotides prepared based on the nucleotide sequence of the known purR gene as primers, and the chromosomal DNA from a microorganism having a purine operon, or the like as a template. Furthermore, the purR gene can also be obtained by hybridization using an oligonucleotide probe based on the nucleotide sequence of the known purR gene of a chromosomal DNA library of microorganisms having purine operon, or the like. The nucleotide sequence of the purR gene of the *Bacillus subtilis* 168 Marburg strain has been reported (GenBank Accession No. D26185 (the coding region is the nucleotide numbers 118041-118898) and NC_000964 (the coding region is the nucleotide numbers 54439-55296)). The nucleotide sequence of the purR gene and the amino acid sequence encoded by the gene are shown in SEQ ID NOS: 51 and 52 (also disclosed in US2004-0166575A).

Primers for cloning the purR gene are not particularly limited as long as they can function in PCR to amplify the purR gene, and specific examples thereof include oligonucleotides having the nucleotide sequences of SEQ ID NO: 59 (GAAGTTGATGATCAAAA) and SEQ ID NO: 60 (ACATATTGTTGACGATAAT).

A purR gene which can be used to prepare a disrupted-type purR gene does not necessarily contain the full length purR gene; a fragment of the purR gene having a length sufficient to disrupt the purR gene may also be used. Furthermore, a bacterium which can be used to obtain the gene for preparing a disrupted-type purR gene is not particularly limited so long as it has a gene which is sufficiently homologous to cause homologous recombination with the purR gene on the chromosome of the *Bacillus* bacterium. However, it is preferable to employ a gene derived from a microorganism which is identical to the targeted *Bacillus* bacterium.

The DNA which is capable of inducing homologous recombination with the purR gene on the chromosome of the *Bacillus* bacterium may be a DNA encoding a protein having an amino acid sequence of SEQ ID NO: 52, wherein one or several, for example, 1 to 50, preferably 1 to 30, and more preferably 1 to 10 amino acids are substituted, deleted, inserted or added.

A DNA which is capable of inducing homologous recombination with the purR gene on the chromosome of the *Bacillus* bacterium may also be a DNA having homology of not less than 70%, preferably not less than 80%, more preferably not less than 90%, and still more preferably not less than 95% to the nucleotide sequence of SEQ ID NO: 51. Such a DNA may also be a DNA that is able to hybridize under stringent conditions with the DNA having the nucleotide sequence of SEQ ID NO: 51. An example of stringent conditions includes washing at 1×SSC and 0.1% SDS, preferably 0.1×SSC and 0.1% SDS at 60° C.

Examples of a marker gene include drug-resistance genes such as the spectinomycin-resistance gene and kanamycin-resistance gene. A spectinomycin-resistance gene derived from *Enterococcus faecalis* can be obtained by preparing plasmid pDG1726 from *Escherichia coli* ECE101 strain, which is commercially available from the *Bacillus* Gentech Stock Center (BGSC), and removing a cassette portion from the plasmid. An erythromycin-resistance gene of *Staphylococcus aureus* can be obtained by preparing plasmid pDG646 from *Escherichia coli* ECE91 strain, commercially available from BGSC, and removing a cassette portion from the plasmid. Furthermore, a kanamycin-resistance gene derived from *Streptococcus faecalis* can be obtained by preparing plasmid pDG783 from *Escherichia coli* ECE94 strain and removing a cassette portion from the plasmid.

When a drug-resistance gene is used as the marker gene, a purR gene-disrupted strain can be obtained by inserting the drug-resistance gene at a suitable site in the purR gene on the plasmid, transforming a bacterium with the resulting plasmid, and selecting transformants which show drug resistance. Disruption of the purR gene on the chromosome can be confirmed by analyzing the purR gene on the chromosome or a marker gene by Southern blotting or PCR. Incorporation of the above-described spectinomycin-resistance gene, erythromycin-resistance gene, or kanamycin-resistance gene into the chromosomal DNA can be confirmed by PCR using primers capable of amplifying these genes.

Expression of the purine operon is known to be controlled by a terminator-antiterminator sequence (hereinafter, referred to as an "attenuator sequence") positioned downstream of the promoter (Ebbole, D. J. and Zalkin, H., J. Biol. Chem., 1987, 262, 8274-8287; Ebbole, D. J. and Zalkin, H., J. Biol. Chem., 1988, 263, 10894-10902; Ebbole, D. J. and Zalkin, H., J. Bacteriol., 1989, 171, 2136-2141) (see FIG. 1). Accordingly, the expression of the purine operon can be enhanced by deleting the attenuator sequence. The attenuator sequence can be deleted by the same method used for disrupting the purR gene.

To further increase the transcription of the purine operon, the above-described methods may be combined. For example, the purine operon from which the attenuator sequence has been deleted may be amplified with a plasmid, or multiple copies of such a purine operon may be introduced into the chromosome, in a strain in which the purR gene is disrupted.

Enhancing the activity of an enzyme involved in purine biosynthesis may also be achieved by eliminating the regulation of such an enzyme, for example, by eliminating feedback inhibition of such an enzyme (WO 99/03988).

The ability to produce a purine-derived substance may also be enhanced by attenuating the uptake of purine-derived substances by the cell. For example, the uptake of purine nucleosides by the cell may be attenuated by blocking a reaction involved in the uptake of purine nucleosides by the cell. An example of a reaction involved in the uptake of purine nucleosides includes reactions catalyzed by nucleoside permeases.

Furthermore, the ability to produce a purine-derived substance may also be enhanced by decreasing an activity of an enzyme involved in degradation of purine-derived substances. An example of such an enzyme includes purine nucleoside phosphorylase.

Purine nucleotides biosynthesized from PRPP by the enzymes involved in purine biosynthesis are dephosphorylated to purine nucleosides. To efficiently produce purine nucleosides, it is preferable to decrease an activity of purine nucleoside phosphorylases that degrade purine nucleosides into hypoxanthine and the like. That is, it is preferable to decrease or eliminate an activity of a purine nucleoside phosphorylase that employs purine nucleosides, such as inosine, as substrates.

Specifically, this can be achieved by disrupting the deoD gene and pupG gene encoding purine nucleoside phosphorylase in a *Bacillus* bacterium. The *Bacillus* bacterium of the present invention may be modified by separately or simultaneously disrupting the deoD gene and pupG gene. The deoD gene and pupG gene from *Bacillus* bacterium (deoD: GenBank Accession No. NC_000964 (SEQ ID NO: 55), pupG: GenBank Accession No. NC_000964 (SEQ ID NO. 53)) may be employed, and disruption of these genes can be performed in the same way as the disruption of the purR gene as described above.

The ability to produce a purine-derived substance may also be enhanced by decreasing an activity of inosine monophosphate (IMP) dehydrogenase. An example of a gene encoding IMP dehydrogenase includes a guaB gene. An example of the guaB gene includes the gene having the nucleotide sequence registered as Accession No. NC_000964(15913 . . . 17376)in GenBank (SEQ ID NO: 61).

The ability to produce a purine-derived substance may also be enhanced by amplifying a gene encoding a protein having an activity to excrete purine-derived substances. An example of a bacterium in which such a gene has been amplified includes a *Bacillus* bacterium in which the rhtA homolog gene has been amplified (JP2003-219876A).

The microorganism used in the present invention may be modified to produce a nucleoside or nucleotide by disrupting a gene encoding the corresponding nucleosidase or nucleotidase. The precursors and their related substances in the biosynthetic system of nucleoside or nucleotide may be produced by imparting an auxotrophy for inosine to the bacterium.

(II) Modification to Enhance an Activity of an Enzyme of the Oxidative Pentosephosphate Pathway.

The *Bacillus* bacterium of the present invention can be obtained by modifying a bacterium having the ability to produce a purine-derived substance as described above to enhance an activity of an enzyme of the oxidative pentosephosphate pathway. The modification to impart the ability to produce a purine-derived substance and the modification to enhance the activity of an enzyme of oxidative pentosephosphate pathway may be performed in any order.

Herein, the term "oxidative pentosephosphate pathway" means the pathway in which glucose that has been taken into the cell is phosphorylated by glucose kinase to glucose-6-phosphate, and glucose-6-phosphate is oxidatively converted to ribose-5-phosphate. Specific examples of an enzymes of oxidative pentosephosphate pathway include glucose-6-phosphate dehydrogenase (EC: 1.1.1.49), 6-phosphate-gluconate dehydrogenase (EC: 1.1.1.44), and ribose-5-phosphate isomerase (EC: 5.3.1.6). Among these enzymes, it is preferable that the activity of one or both of glucose-6-phosphate dehydrogenase and ribose-5-phosphate isomerase is enhanced in the *Bacillus* bacterium of the present invention.

It is preferable that the activity of an enzyme of oxidative pentosephosphate pathway is enhanced as compared to a wild-type strain or an unmodified strain. The increase in an activity of such an enzyme can be measured by the following methods. For example, the enzymatic activity of glucose-6-phosphate dehydrogenase can be measured by measuring the production of NADPH as described in (1) of Example 6, and the enzymatic activity of ribose-5-phosphate isomerase can be measured by measuring the production of ribulose-5-phosphate as described in (2) of Example 6.

The activity of the enzyme of the oxidative pentosephosphate pathway can be enhanced by amplifying a gene encoding such an enzyme. The genes to be amplified are not specifically limited as long as they encode a protein having an activity of an enzyme involved in the oxidative pentose-phosphate pathway. For example, genes derived from *Bacillus* bacterium may be employed.

An example of a gene encoding glucose-6-phosphate dehydrogenase includes a gene encoding the glucose-6-phosphate dehydrogenase of *Bacillus subtilis* which has an amino acid sequence of SEQ ID NO: 48, and preferably includes a gene having the nucleotide sequence of SEQ ID NO: 47 (the zwf gene: GenBank Accession No. NC_000964). The zwf gene is present at 212 degrees on the chromosome of *Bacillus subtilis*.

An example of ribose-5-phosphate isomerase includes a gene encoding a protein having amino acid sequence of SEQ ID NO: 50, and preferably includes a gene having a nucleotide sequence of SEQ ID NO: 49 (the ywlF gene: GenBank Accession No. NC_000964). The ywlF gene is present at 324 degrees on the chromosome of *Bacillus subtilis* in the vicinity of the glyA gene that encodes serine hydroxymethyl transferase. Ribose-5-phosphate isomerases include the enzyme known as ribose-5-phosphate epimerase.

Genes encoding an enzyme of the oxidative pentosephosphate pathway may be derived from a bacterium other than *Bacillus* bacterium, and may also be derived from plants or animals. A gene whose nucleotide sequence is already known, and a gene obtained by isolating a gene encoding a protein having an activity of an enzyme involved in the oxidative pentosephosphate pathway based on homology with the known nucleotide sequence from the chromosome of microorganisms, plants, and animals, and followed by sequence determination may be employed. A gene synthesized based on the nucleotide sequence may also be employed. Such genes may be obtained by amplifying a region containing a promoter and ORF by hybridization or PCR. Sequence information can be obtained from a public database such as GenBank.

In a *Bacillus* bacterium, the intracellular activity of an enzyme can be enhanced by increasing the expression of the gene encoding the enzyme. The expression of the gene can be increased by increasing the copy number of the gene. For example, a fragment of a gene encoding the enzyme can be ligated to a vector that functions in a *Bacillus* bacteria, preferably a multi-copy vector, to prepare a recombinant DNA. The obtained recombinant DNA is used to transform the *Bacillus* bacterium.

A gene derived from a *Bacillus* bacterium and a gene derived from other organisms such as *Escherichia* bacterium may be employed so long as the gene functions in *Bacillus* bacterium.

The targeted gene may be obtained, for example, by PCR using a chromosomal DNA of a *Bacillus* bacterium as a template (PCR: polymerase chain reaction; White, T. J. et al., Trends Genet., 1989, 5, 185-189). Chromosomal DNA may be prepared from a bacterium serving as a DNA donor by the method of Saito and Miura (see H. Saito and K. Miura, Biochem. Biophys. Acta, 1963, 72, 619-629, Manual of Bioengineering Experiments, ed. by the Japan Bioengineering Society, pp. 97-98, Baifukan, 1992). The primers used in PCR can be designed based on the known sequence of the gene of *Bacillus* bacteria or based on the sequence conserved between the genes from different organisms.

Examples of vectors capable of autonomous replicating used for introducing target genes into a *Bacillus* bacterium include pUB110, pC194, and pE194. Furthermore, examples of vectors for introducing target genes into a chromosomal DNA include vectors for *E. coli* such as pHSG398 (Takara-Bio Co. (K.K.)) and pBluescript SK (Stratagene).

To prepare a recombinant DNA by ligating a target gene and marker into a vector functioning in *Bacillus* bacterium, the vector is digested with suitable restriction enzymes corresponding to the ends of the target gene. For ligation, a ligase such as T4 DNA ligase can be employed.

The transformation methods as described above may be employed to introduce the recombinant DNA prepared as described above into a *Bacillus* bacterium. For example, competent cells can be prepared from cells at the growing stage to introduce the DNA (Dubnau, D., and Davidoff-Abelson, R., J. Mol. Biol., 1971, 56, 209-221). Another method where a recombinant DNA is incorporated into DNA-recipient cells in the form of protoplast or spheroplast that readily incorporates the recombinant DNA (Chang, S. and Cohen, S. N., Molec. Gen. Genet., 1979, 168, 111-115) may also be used.

The copy number of the target gene can also be increased by integrating the gene in multiple copies into the chromosomal DNA of a *Bacillus* bacterium. Multiple copies of a target gene can be integrated into the chromosomal DNA of a *Bacillus* bacterium by recombination using a sequence present on the chromosomal DNA in multiple copies as a target. Examples of the sequences that are present in multiple copies on chromosomal DNA include transposons, repeat sequences, and inverted repeats which are present on the ends of transposable elements.

In addition to the above-described gene amplification, the activity of the target enzyme can also be enhanced by replacing the expression regulatory sequence of the promoter of the target gene on the chromosomal DNA or plasmid with a stronger one. The strength of a promoter is defined as the frequency of initiation acts of RNA synthesis. Goldstein (Prokaryotic promoters in biotechnology. Biotechnol. Annu. Rev., 1995, 1, 105-128) discloses methods of evaluating the strength of promoters and provides examples of strong promoters. As disclosed in WO 00/18935, a promoter can be made stronger by replacing several nucleotides in the promoter region of the target gene. Furthermore, substitution of nucleotides in the spacer region between a ribosome binding site (RBS) and a start codon, particularly substitution of several nucleotides in the sequence immediately upstream of a start codon, is known to strongly affect the translation efficiency of mRNA. The modification of the expression regulatory sequence may be combined with increasing the copy number of the target gene.

Examples of promoters that function in *Bacillus* bacteria include the veg promoter, spac promoter, and xyl promoter.

So long as the enzymatic activity of the oxidative pentosephosphate pathway is maintained, the gene encoding the enzyme of the oxidative pentosephosphate pathway may encode a protein having an amino acid sequence of SEQ ID NO: 48 or 50, wherein one or several amino acid are substituted, deleted, inserted, or added at one or multiple positions. Herein, although the term "several" depends on the type and position of the amino acid residues within the three dimensional structure of the protein; it means 1 to 30, preferably 1 to 20, and more preferably, 1 to 10.

The above-described mutation in the amino acid sequence of SEQ ID NO: 48 or 50 protein is preferably a conservative mutation which does not impair the enzymatic activity. A substitution means a mutation whereby at least one residue in the amino acid sequence is removed and one or more residues are inserted at that location. The conservative substitutions include: substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr and substitution of Met, Ile, or Leu for Val.

The above-described DNA encoding a protein substantially identical to the wild-type enzyme of the oxidative pentosephosphate pathway can be obtained by a site-specific mutation method, for example, in which the nucleotide sequence encoding the enzyme is modified so as to substitute, delete, insert, add, or invert an amino acid residue at a specific site. The above-described modified DNA may also be obtained by a conventional mutation treatment. Examples of mutation treatments include in vitro treatment of a wild-type DNA with hydroxylamine and subjecting a microorganism carrying a wild-type DNA, such as an *Escherichia* bacterium transformed with the DNA, to UV irradiation or treatment with a mutagenic agent commonly employed in mutation treatments, such as N-methyl-N'-nitro-N-nitrosoguanidine (NTG) or nitrous acid.

The DNA having the above-described mutation is induced in a suitable cell and the activity of the expression product is examined to obtain a DNA encoding a protein substantially identical to a wild-type enzyme of the oxidative pentosephosphate pathway. Furthermore, a DNA encoding such a homolog can be obtained by hybridizing under stringent conditions with a probe having a part or all of the nucleotide sequence of SEQ ID NO: 47 or 49, and wherein the DNA encodes a protein having an activity of an enzyme involved in the oxidative pentosephosphate pathway, and is from a cell having the DNA encoding such a homolog enzyme. Herein, the term "stringent conditions" means conditions under which a specific hybrid can be formed and non-specific hybrids cannot be formed. Examples thereof include conditions under which DNA fragments having a high homology, for example, not less than 80%, preferably not less than 90%, and more preferably not less than 95% hybridize with each other, and DNA fragments having a lower homology do not hybridize. A specific example thereof includes a condition of washing in Southern hybridization such as a condition comprising washing at 1×SSC and 0.1% SDS, preferably 0.1×SSC and 0.1% SDS at 60° C.

A portion of the nucleotide sequence of SEQ ID NO: 47 or 49 may be used as a probe. Such a probe can be prepared by PCR using oligonucleotides based on the nucleotide sequence of SEQ ID NO: 47 or 49 as primers and a DNA fragment containing the nucleotide sequence of SEQ ID NO: 47 or 49 as a template. When a DNA fragment of about 300 bp in length is used as a probe, the hybridization conditions may be washing at 50° C., 2×SSC, 0.1% SDS.

A DNA encoding a protein substantially identical to a wild-type enzyme of the oxidative pentosephosphate pathway may encode a protein having a homology of not less than 80%, preferably not less than 90%, and more preferably not less than 95% to the amino acid sequence of SEQ ID NO: 48 or 50, and which has an activity of an enzyme of the oxidative pentosephosphate pathway.

<2>Method for Producing a Purine-Derived Substance

The *Bacillus* bacterium of the present invention efficiently produces a purine-derived substance. Accordingly, purine-derived substances such as purine nucleosides and purine nucleotides can be produced in a medium or in the bacterial cells by culturing the *Bacillus* bacterium of the present invention in a suitable medium.

The medium used for culturing the *Bacillus* bacterium of the present invention may be a common nutrient medium containing a carbon source, nitrogen source, inorganic salt source, and, if necessary, trace amount of organic nutrients such as amino acids and vitamins. The culture may be performed according to conventional methods. Either a synthetic or natural medium may be used. The carbon source and nitrogen source added to the medium are not particularly limited so long as they can be assimilated by the *Bacillus* bacterium to be cultured.

The carbon source may be a sugar such as glucose, fructose, sucrose, maltose, mannose, galactose, arabinose, xylose, trehalose, ribose, starch hydrolysis products, and molasses; an alcohol such as glycerol or mannitol; an organic acid such as gluconic acid, acetic acid, citric acid, maleic acid, fumaric acid, and succinic acid. These carbon sources may be used singly or in combination.

A nitrogen source may be ammonia, ammonium sulfate, ammonium carbonate, ammonium chloride, ammonium phosphate, ammonium acetate, other ammonium salts, nitrates, soybean hydrolysis products, and other forms of organic nitrogen may also be used.

Trace amounts of organic nutrients, such as amino acids, vitamins, fatty acids, nucleic acid, peptones containing these compounds, casamino acids, yeast extract, and soy protein decomposition products, may be used. When a mutant strain auxotrophic for an amino acid, nucleoside, or the like is cultured, it is necessary to supplement with the nutrient required by the strain.

Examples of inorganic salts include phosphate salts, magnesium salts, calcium salts, iron salts, manganese salts, and the like.

The culture conditions depend on the type of a *Bacillus* bacterium to be cultured. In the case of *Bacillus subtilis*, culture may be conducted at a fermentation temperature of 20 to 50° C. with a regulated pH of 4 to 9 and with aeration. When the pH decreases during the culture, the medium may be neutralized with an alkali such as ammonium gas. Culture may be conducted for 40 hours to 3 days to produce a purine-derived substance in the culture medium.

The purine-derived substance, such as inosine, which is produced in the culture medium can be collected by a conventional method. For example, purine nucleosides including inosine and guanosine can be collected by precipitation, ion-exchange chromatography, or the like.

Furthermore, the inosine or guanosine produced by the method of the present invention may be subjected to a reaction with purine nucleoside phosphorylase and phosphoribosyl transferase to obtain 5'-inosinic acid and 5'guanylic acid, respectively.

Furthermore, purine nucleotides (nucleoside-5'-phosphoric esters) can be produced by subjecting the purine nucleoside produced by the method of the present invention to a reaction with a bacterium which has the ability to produce nucleoside-5'-phosphoric ester, or with an acid phosphatase in the presence of a phosphate donor selected from the group consisting of polyphosphoric acid, phenyl phosphate, and carbamyl phosphate. The bacterium which has the ability to produce nucleoside-5'-phosphoric esters is not particularly limited so long as it has the ability to produce nucleoside-5'-phosphoric esters, and examples thereof include a bacterium described in WO96/37603, *Escherichia blattae* JCM 1650, *Serratia ficaria* ATCC 33105, *Klebsiella planticola* IFO 14939 (ATCC 33531), *Klebsiella pneumoniae* IFO 3318 (ATCC 8724), *Klebsiella terrigena* IFO 14941 (ATCC 33257), *Morganella morganii* IFO 3168, *Enterobacter aerogenes* IFO 12010, *Enterobacter aerogenes* IFO 13534 (ATCC 13048), *Chromobacterium fluviatile* IAM 13652, *Chromobacterium violaceum* IFO 12614, *Cedecea lapagei* JCM 1684, *Cedecea davisiae* JCM 1685, and *Cedecea neteri* JCM 5909, disclosed in JP07-231793A.

An example of acid phosphatase (EC 3.1.3.2) which can be used for producing purine nucleotides includes the one disclosed in JP2002-000289A, U.S. Pat. No. 6,010,851, U.S. Pat. No. 6,015,697, WO01/18184, and preferably includes a mutant acid phosphatase having an enhanced affinity for nucleosides (U.S. Pat. No. 6,015,697), a mutant acid phosphatase with no nucleotidase activity (WO96/37603), and a mutant acid phosphatase with no phosphoric ester hydrolytic activity (U.S. Pat. No. 6,010,851).

EXAMPLES

The present invention is described in more detail by reference to the following non-limiting examples.

Example 1

<Construction and Culture Evaluation of Purine Nucleoside Phosphorylase-Disrupted Strain>

(1) Construction of a Purine Nucleoside Phosphorylase (pupG)-Disrupted Strain

A disrupted-type pupG gene was introduced into a recombinant KMBS16 strain (2004-0166575A) which is derived from *Bacillus subtilis* (*B. subtilis* 168 Marburg strain; ATCC6051) and in which the purine operon repressor gene (purR), succinyl-AMP synthase gene (purA), and purine nucleoside phosphorylase gene (deoD) are disrupted, as follows.

(i) Cloning of the 5'-End Region of the pupG Gene

Based on the information from GenBank (Accession No. NC_000964), the primers having the following nucleotide sequence were designed for PCR:

ATTGCACGGCCGTTCGTCGG (SEQ ID NO: 1)

cgcagatctCCGGATTTTCGATTTCGTCC (SEQ ID NO: 2; The nucleotide sequence indicated by lower case letters is a tag containing a BglII site.)

Using a chromosomal DNA from *B. subtilis* 168 Marburg strain as a template and the above-described primers, PCR was conducted (94° C., 30 seconds; 55° C., 1 minute; 72° C., 2 minutes; 30 cycles; Gene Amp PCR System Model 9600 (Perkins Elmer)), to amplify a fragment containing a region upstream of a translation initiation codon of the pupG gene (about 610 bp) and its downstream region (about 120 bp).

The amplified fragment was purified by phenol-chloroform extraction and ethanol precipitation. Perfectly Blunt Cloning Kit (NOVAGEN) was employed for cloning the fragment into the pT7Blue plasmid, which was included in the kit. Both ends of the multicloning site of this plasmid are EcoRI and HindIII. A plasmid in which the pupG gene is inserted in a direction so that the upstream region of the pupG gene is on the EcoRI side was selected and named pKM48.

(ii) Cloning of the 3'-End Region of the pupG Gene

Based on the information from GenBank (Accession No. NC_000964), primers having the following nucleotide sequence were designed for PCR:

CAAAGATCTGTCCAGCCTGG (SEQ ID NO: 3 cgcctgcagTGCCTTTATCTAAAGCTTCC (SEQ ID NO: 4; The nucleotide sequence indicated by lower case letters is a tag containing a PstI site.)

Using a chromosomal DNA from *B. subtilis* 168 Marburg strain as a template and the above-described primers, PCR was conducted (94° C., 30 seconds; 55° C., 1 minute; 72° C., 2 minutes; 30 cycles; Gene Amp PCR System Model 9600 (Perkins Elmer)), to amplify a fragment containing a region upstream of the translation stop codon (about 340 bp) and its downstream region (about 400 bp).

In the same manner as the cloning of the 5'-end region of the pupG gene, the amplified fragment was cloned into pT7Blue plasmid, and thereby a plasmid in which the pupG gene is inserted in a direction so that the downstream region of the pupG gene is on the EcoRI side was selected and named pKM49.

(iii) Cloning of ΔpupG Fragment

After digesting the pKM49 with SpeI, it was blunted with Klenow fragment and further digested with PstI, to excise a DNA fragment of about 740 bp. This fragment was ligated using T4 DNA ligase to a plasmid fragment which was obtained by treating the pKM48 with BglII, blunting with Klenow fragment and digesting with PstI, and thereby the plasmid pKM75 was obtained. This plasmid has about 1,470 bp insert comprising the disrupted-type pupG fragment in which about 360 bp of the pupG structural gene had been deleted.

(iv) Construction of a Plasmid to Disrupt the pupG Gene

An insert was excised from pKM75 by treating the plasmid with SacI and PstI. The obtained fragment was ligated using T4 DNA ligase to a recombination vector pJPM1 (Mueller et al., J. Bacteriol., 1992, 174, 4361-4373) that had been treated with the same enzymes, and thereby a plasmid pKM76 was obtained.

Competent cells of the KMBS16 strain prepared by the method of Dubnau and Davidoff-Abelson (J. Mol. Biol., 1971, 56, 209-221) were transformed with the plasmid pKM76, and the colonies (single-crossover recombinants) that were capable of growing on LB agar plate containing 2.5 µg/mL of chloramphenicol were selected.

The obtained single-crossover recombinants were inoculated into 10 mL of LB medium and successively subcultured for several days at 37° C. Colonies exhibiting chloramphenicol sensitivity were selected on a plate of LB medium including chloramphenicol. Chromosomal DNA was prepared from the obtained chloramphenicol-sensitive colonies. PCR was conducted in the same manner as described above using primers of SEQ ID NOS: 5 and 6. Bacterial strains (purR::spc purA::erm deoD::kanΔpupG) in which the pupG gene on the chromosome had been replaced with the disrupted-type pupG gene (ΔpupG) by double-crossover recombination were identified. The obtained strain was named KMBS93.

GGTCTGAGCTTTGCGAACC (SEQ ID NO: 5)

CGCCTGCAGTGCCTTTATCTAAAGCTTCC (SEQ ID NO: 6)

(2) The disrupted-type pupG gene was introduced into the recombinant KMBS13 strain (US2004-0166575A) which is derived from *Bacillus subtilis* (*B. subtilis* strain 168 Marburg; ATCC6051) and in which the purine operon repressor gene (purR) and succinyl-AMP synthase gene (purA) are disrupted, as follows.

Competent cells of the KMBS13 strain prepared as described above were transformed with plasmid pKM76, and the colonies (single-crossover recombinants) that were capable of growing on an LB agar plate containing 2.5 µg/mL of chloramphenicol were selected.

The obtained single-crossover recombinants were inoculated into 10 mL of LB medium and successively subcultured for several days at 37° C. Colonies exhibiting chloramphenicol sensitivity were selected on a plate of LB medium including chloramphenicol. Chromosomal DNA was prepared from the obtained chloramphenicol-sensitive colonies. PCR was conducted in the same manner as described above using primers of SEQ ID NOS: 5 and 6. Bacterial strains (purR::spc purA::erm ΔpupG) in which the pupG gene on the chromosome had been replaced with the disrupted-type of pupG gene (ΔpupG) by double-crossover recombination were identified. The obtained double-recombinant strain was named KMBS113.

(3) Purine Nucleoside Production by the pupG Gene-Disrupted Strains

The pupG gene-disrupted strains (KMBS93 and KMBS113) and control strain (KMBS16) were uniformly spread over PS plate medium (30 g/L of soluble starch, 5 g/L of yeast extract, 5 g/L of polypeptone, 20 g/L of agar, adjusted to pH 7.0 with KOH) and cultured overnight at 34° C. One-eighth of the bacterial cells on the plate were inoculated into 20 mL of fermentation medium contained in a 500 mL capacity Sakaguchi flask. Subsequently, calcium carbonate was added at 50 g/L and culture was performed at 34° C. with shaking. Sampling was conducted at the time point of 100 hours from the start of culturing, and the amounts of inosine and hypoxanthine accumulated in the culture medium were measured by conventional methods. A large amount of hypoxanthine was detected in the culture medium of the control KMBS16 strain. However, the hypoxanthine accumulation by the pupG gene-disrupted strains KMBS93 and KMBS113 was extremely low, and no clear peak was detected by HPLC (Table 1). On the other hand, the inosine accumulation by the strains KMBS93 and KMBS113 was greater than that of the control strain KMBS16.

Composition of the fermentation medium:

| Glucose | 80 g/L |
| --- | --- |
| KH$_2$PO$_4$ | 1 g/L |
| NH$_4$Cl | 32 g/L |
| Mameno (T-N)* | 1.35 g/L |
| DL-methionine | 0.3 g/L |
| L-tryptophan | 0.02 g/L |
| Adenine | 0.1 g/L |
| MgSO$_4$ | 0.4 g/L |
| FeSO$_4$ | 0.01 g/L |
| MnSO$_4$ | 0.01 g/L |
| GD113 | 0.01 mL/L |
| (adjusted to pH 7.0 with KOH) | |
| Calcium carbonate | 50 g/L |

*Protein hydrolysis product

TABLE 1

| B. subtilis strain | OD562 | Hypoxanthine g/L | Inosine g/L |
| --- | --- | --- | --- |
| KMBS16 | 8.84 | 2.27 | 1.65 |
| KMBS93 | 7.02 | ND*[1] | 4.49 |
| KMBS113 | 7.02 | ND*[1] | 5.43 |

*[1]No clear peak could be detected under the HPLC conditions employed.

Example 2

(1) Introduction of a Mutant guaB Gene

A guaB (A1) mutation which results in replacement of the Alanine at position 226 in SEQ ID NO: 62 with Valine in the IMP dehydrogenase gene (guaB) was introduced into a recombinant KMBS113 strain that was derived from Bacillus subtilis (B. subtilis strain 168 Marburg; ATCC6051) and in which the purine operon repressor gene (purR), succinyl-AMP synthase gene (purA), and purine nucleosidase phosphorylase gene (pupG) had been disrupted, as follows. The introduction of the guaB(A1) mutation causes a reduction in the enzyme activity of IMP dehydrogenase.

(i) Preparation of a Bacterial Strain in Which a Kanamycin-Resistance Gene was Inserted into the Middle of the Wild-Type guaB Gene Derived from B. subtilis Strain 168 Marburg Strain In amplification of the upstream region of the guaB gene, PCR primers having the nucleotide sequences shown below were designed based on GenBank information (Accession No. NC_000964 and V01547):

cgcggatccGGCTTAACGTTCGACGATGTGCTGC (SEQ ID NO: 7; The nucleotide sequence indicated by lower case letters is a tag containing the BamHI site);

gctttgcccattctatagatatat-tGAGTCATTGTATCGCCAGTTACACC (SEQ ID NO: 8; The nucleotide sequence indicated by lower case letters is the sequence upstream of the promoter of the kanamycin-resistance gene (kan) which was cloned into pDG783 (BGSC)).

PCR was conducted (94° C., 30 seconds; 55° C., 1 minute; 72° C., 1 minute; 30 cycles; Gene Amp PCR System Model 9600 (made by Perkins Elmer)) using the above-described primer and a template of a chromosomal DNA of B. subtilis 168 Marburg strain to amplify a fragment (about 710 bp) of the 5'-end of the guaB gene.

In amplification of the 3'-end of guaB gene, PCR primers having the nucleotide sequences shown below were designed based on GenBank information (Accession No. NC_000964 and V01547):

cctagatttagatgtctaaaaagctGT-GATTGTTATCGATACAGCTCACG (SEQ ID NO: 9; the nucleotide sequence indicated by lower case letters is the sequence downstream of the structural gene of the kanamycin-resistance gene (kan) which was cloned into pDG783 (BGSC);

cgcgaattcGTAATCTGTACGTCATGCGGATGGC (SEQ ID NO: 10: the nucleotide sequence represented in lower case letters is a tag containing the EcoRI site).

PCR was conducted (94° C., 30 seconds; 55° C., 1 minute; 72° C., 1 minute; 30 cycles; Gene Amp PCR System Model 9600 (Perkins Elmer)) using the above-described primers and a template of chromosomal DNA of B. subtilis 168 Marburg strain to obtain an amplified fragment (about 730 bp) of 3'-end of the guaB gene.

In amplification of the 3'-end of kan gene by PCR, PCR primers having the following nucleotide sequence were prepared based on information from GenBank (Accession Nos. V01277 and NC_000964):

ggtgtaactggcgatacaatgact-cAATATATCTATAGAATGGGCAAAGC (SEQ ID NO: 11; the nucleotide sequence indicated by lower case letters is complementary to the 3'-end region of the sequence of the guaB upstream region in SEQ ID NO: 8;);

cgtgagctgtatcgataacaatca-cAGCTTTTAGACATCTAAATCTAGG (SEQ ID NO: 12;

the nucleotide sequence indicated by lower-case letters is complementary to the 3'-end region of the guaB downstream sequence in SEQ ID NO: 9).

PCR (94° C., 30 seconds; 55° C., 1 minute; 72° C., 1 minute; 30 cycles; Gene Amp PCR System Model 9600 (Perkins Elmer)) was conducted using the above-described primers and a template of the plasmid DNA containing a kanamycin-resistance gene (kan), such as pDG783, to amplify a fragment of about 1,150 bp which contains the kan gene.

In amplification of the guaB region inserted with the kan gene by recombinant PCR, the three DNA fragments amplified as described above were purified using MicroSpin Column S-400 (Amersham Pharmacia Biotech), a suitable quantity of the mixture was used as a template, and the primers of SEQ ID NOS: 7 and 10 were used, and PCR (94° C., 30 seconds; 55° C., 1 minute; 72° C., 2 minutes; 30 cycles; Gene Amp PCR System Model 9600 (made by Perkins Elmer)) was conducted, and thereby an amplified fragment of the guaB gene into which a kan gene had been inserted was obtained.

The target fragment of the guaB gene into which a kan gene had been introduced (guaB::kan) was extracted from the gel following agarose gel electrophoresis. Competent cells of B. subtilis strain prepared as described above were transformed with the DNA fragment and colonies that were capable of growing on an LB agar plate containing 2.5 µg/mL of kanamycin and 20 µg/mL of guanine were selected. Chromosomal DNA was prepared from these colonies and PCR was conducted using primers of SEQ ID NOS: 7 and 10 to identify a bacterial strain in which the native guaB region on the chromosome had been replaced with a guaB gene in which the internal sequence had been inserted with a kanamycin-resistance gene (guaB::kan) by double-crossover recombination. The recombinant strain thus obtained was guanine-auxotroph; the strain was named KMBS193.

(ii) Preparation of a Bacterial Strain Which is Derived from B. subtilis 168 Marburg and in Which a guaB Mutation (A1) is Introduced In amplification of the 5'-end of guaB gene, PCR primers having the following nucleotide sequences were designed based on the information from GenBank (Accession No. NC_000964):

CATAAAATGTACGCATAGGCCATTC (SEQ ID NO: 13);

TTGTATCGCCAGTTACACCAACTaC-CGCGCCAACGATCAGGCGGCC (SEQ ID NO: 14: the nucleotide indicated by a lower-case letter is a mutation point).

PCR (94° C., 30 seconds; 55° C., 1 minute; 72° C., 1 minute; 30 cycles; Gene Amp PCR System Model 9600 (Perkins Elmer)) was conducted using the above-described primers and a template of the chromosomal DNA of B. subtilis 168 Marburg strain to amplify a fragment (about 1,210 bp) containing the 5'-end region and the upstream region of the guaB gene.

Then, the 3'-end of guaB gene was amplified. Based on the information from GenBank (Accession No. NC_000964), PCR primers having the following nucleotide sequences were prepared:

GGCCGCCTGATCGTTGGCGCGGtAGTTG-GTGTAACTGGCGATACAA (SEQ ID NO: 15: the nucleotide indicated by a lower-case letter is a mutation point; this primer is complementary to SEQ ID NO: 14);

CCTTGATCAATTGCTTCCAATAACAG (SEQ ID NO: 16)

PCR (94° C., 30 second; 55° C., 1 minute; 72° C., 1 minute; 30 cycles; Gene Amp PCR System Model 9600 (made by Perkins Elmer)) was conducted using the above-described primers and a template of the chromosomal DNA of B. subtilis 168 Marburg strain to amplify a fragment (about 1,220 bp) containing 3'-end and downstream region of the guaB gene.

In amplification of the guaB region into which a guaB (A1) mutation had been introduced by recombinant PCR, the two DNA fragments obtained as described above were subjected to agarose gel electrophoresis and the target DNA fragments were purified. A mixture of suitable quantities of the two DNA fragments was employed as a template, SEQ ID NOS: 13 and 16 were employed as primers, and PCR (94° C., 30 second; 55° C., 1 minute; 72° C., 2 minutes; 30 cycles; Gene Amp PCR System Model 9600 (made by Perkins Elmer)) was conducted to amplify a fragment of the guaB gene into which a guaB (A1) mutation had been introduced.

The target fragment of the guaB gene (guaB (A1)) into which a guaB (A1) mutation had been introduced was extracted from the gel following agarose gel electrophoresis. Competent cells of KMBS193 prepared as described above were transformed with the DNA fragment, and colonies that were capable of growing on minimal medium agar plate were selected. Chromosomal DNA was prepared from these colonies and PCR was conducted with primers of SEQ ID NOS: 13 and 16 to identify bacterial strains in which the guaB::kan region on the chromosome had been replaced with a guaB region containing a guaB (A1) mutation by double-crossover recombination. The recombinant thus obtained was not guanine-auxotroph; and the strain was named YMBS9.

(iii) Preparation of a Bacterial Strain Derived from Inosine-Producing Bacterium KMBS113 and into Which a guaB Mutation (A1) was Introduced Chromosomal DNA of KMBS193 (guaB::kan) was prepared and used to transform competent cells of strain KMBS113 prepared as described above, and colonies that were capable of growing on an LB agar plate containing 2.5 µg/mL of kanamycin and 20 µg/mL of guanine were selected. The obtained strain was auxotrophic for guanine, and named YMBS6 (purR::spc purA::erm ΔpupG guaB::kan trpC2).

Next, a chromosomal DNA of YMBS9 (guaB(A1)) was prepared and used to transform competent cells of strain YMBS6 prepared as described above, and colonies that were capable of growing on a minimal medium agar plate containing 20 µg/mL of adenine were selected. The obtained strain was leaky auxotrophic for guanine, and the strain was named YMBS2 (purR::spc purA::erm guaB(A1) ΔpupG trpC2).

(2) Production of Purine-Derived Nucleic Acid by an Inosine-Producing Strain into Which the guaB Mutation was Incorporated An inosine-producing strain into which guaB (A1) mutation had been incorporated (YMBS2 strain) and a control KMBS113 strain were uniformly spread over PS plate medium (soluble starch 30 g/L, yeast extract 5 g/L, polypeptone 5 g/L, agar 20 g/L, adjusted to pH 7.0 with KOH) and cultured overnight at 34° C. One-eighth of the bacterial cells were inoculated into 20 mL of fermentation medium in a 500 mL capacity Sakaguchi flask. Subsequently, calcium carbonate was added at 50 g/L and each of the bacteria was cultured at 34° C. with shaking. Sampling was conducted at the time point of 96 hours after the start of culturing, and the amounts of inosine and hypoxanthine in the culture medium were measured by conventional methods.

Composition of the fermentation medium:

| | |
|---|---|
| Glucose | 60 g/L |
| KH$_2$PO$_4$ | 1 g/L |
| NH$_4$Cl | 32 g/L |
| Mameno (T-N)* | 1.35 g/L |
| DL-methionine | 0.3 g/L |
| L-tryptophan | 0.02 g/L |
| Adenine | 0.1 g/L |
| MgSO$_4$ | 0.4 g/L |
| FeSO$_4$ | 0.01 g/L |
| MnSO$_4$ | 0.01 g/L |
| GD113 | 0.01 mL/L |
| (adjusted to pH 7.0 with KOH) | |
| Calcium carbonate | 50 g/L |

*Protein hydrolysis product

TABLE 2

| B. subtilis strain | OD610 | Inosine (g/L) | Xanthosine (g/L) |
|---|---|---|---|
| KMBS113 | 17.4 | 3.1 | 0.06 |
| YMBS2 | 6.43 | 3.7 | 0.05 |

Example 3

<Preparation of a Purine Operon-Amplified Strain>

(1) Preparation of Ppur-Disrupted Strain

A strain derived from *Bacillus subtilis* (*B. subtilis* 168 Marburg strain; ATCC6051) and in which purine operon promoter (Ppur) was disrupted was prepared as follows.

(i) Amplification of the Upstream Region of the Ppur by PCR

Based on the information from GenBank (Accession No. NC_000964 and V01277), PCR primers having the following nucleotide sequence were prepared:

cgcggatccTTATTTAGCGGCCGGCATCAGTACG (SEQ ID NO: 17; the nucleotide sequence indicated by lower-case letters is a tag containing a BamHI site);

cgtttgttgaactaatgggtgctttATG-GATAATGTCAACGATATTATCG (SEQ ID NO: 18: the nucleotides indicated by lower-case letters is the sequence of upstream of the promoter of the chloramphenicol-resistance gene (cat) that is cloned into pC194).

PCR was conducted (94° C., 30 seconds; 55° C., 1 minute; 72° C., 1 minute; 30 cycles; Gene Amp PCR System Model 9600 (Perkins Elmer)) using the above-described primers and a template of chromosomal DNA of the *B. subtilis* 168 Marburg strain to amplify a fragment containing the Ppur-35 sequence and the upstream region (about 730 bp).

(ii) Amplification of the Downstream Region of Ppur by PCR

Based on the information from GenBank (Accession No. NC_000964 and V01277), PCR primers having the following nucleotide sequences were prepared:

acagctccagatccatatccttcttCCT-CATATAAATCTTGGGAATATGGC (SEQ ID NO: 19; the nucleotide sequence indicated by lower-case letters is the sequence of downstream region of the structural gene of the chloramphenicol-resistance gene (cat) that is cloned into the pC194 plasmid);

cgcggatccTCTCTCATCCAGCTTACGGGCAAGG (SEQ ID NO: 20; the nucleotide sequence indicated by lower-case letters is a tag containing the BamHI site).

PCR was conducted (94° C., 30 second; 55° C., 1 minute; 72° C., 1 minute; 30 cycles; Gene Amp PCR System Model 9600 (Perkins Elmer)) using the above-described primers and a template of a chromosomal DNA of *B. subtilis* 168 Marburg strain to amplify a fragment containing about 230 bp region upstream of the purE gene translation start codon and its downstream region of about 440 bp.

(iii) Amplification of the Cat Gene by PCR

PCR primers having the following sequences were designed based on the information from GenBank (Accession No. V01277 and NC_000964):

cgataatatcgttgacattatccat-AAAGCACCCATTAGTTCAACAAACG (SEQ ID NO: 21; the nucleotide sequence indicated by lower-case letters is complementary to the 3'-end region of the Ppur upstream region sequence in SEQ ID NO: 18);

gccatattcccaagattatatgaggAA-GAAGGATATGGATCTGGAGCTGT(SEQ ID NO: 22; the nucleotide sequence indicated by lower-case letters is complementary to the 3'-end of the region upstream of translation start codon in the purE gene in SEQ ID NO. 19).

PCR was conducted (94° C., 30 seconds; 55° C., 1 minute; 72° C., 2 minute; 30 cycles; Gene Amp PCR System Model 9600 (made by Perkins Elmer)) using the above-described primers and a template of the plasmid DNA comprising a chloramphenicol-resistance gene (cat), such as pC194, to amplify a fragment of about 980 bp containing the cat gene.

(iv) Amplification of the Ppur Region in Which a Cat Gene is Inserted by PCR

The DNA fragments amplified in the above (i) to (iii) were purified on a MicroSpin Column S-400 (Amersham Pharmacia Biotech), mixed in suitable quantities, and used as templates; primers of SEQ ID NOS: 17 and 20 were employed; and PCR was conducted (94° C., 30 seconds; 55° C., 1 minute; 72° C., 2 minutes; 30 cycles; Gene Amp PCR System Model 9600 (made by Perkins Elmer)), and thereby a fragment of the Ppur region in which a cat gene is inserted was obtained.

(v) Production of a Bacterial Strain in Which Ppur is Disrupted

The DNA fragment of the Ppur region in which cat gene is inserted (Ppur::cat) obtained in the above (iv) was subjected to agarose gel electrophoresis and the fragment was extracted from the gel. DNA fragment purified in this manner was used to transform competent cells of *B. subtilis* prepared as described above, and the colonies that were capable of growing on LB agar plate containing 2.5 μg/mL of chloramphenicol were selected. Chromosomal DNA was prepared from these colonies. Using the PCR fragment described in the above (iv), a bacterial strain in which the chromosomal Ppur region had been replaced with a Ppur region into which cat gene had been inserted (Ppur::cat) by double-crossover recombination was identified. The recombinant strain obtained in this manner was auxotrophic for adenine; and the strain was named KMBS198.

(2) <Preparation of a Purine Operon Promoter Mutant>

A bacterial strain derived from *Bacillus subtilis* (*B. subtilis* 168 Marburg strain; ATCC6051) and modified to change the −10 sequence of Ppur to the similar consensus sequence TATAAT (Ppur1), TATGAT (Ppur3), and TAAAAT (Ppur5), respectively was prepared as follows.

(i) Amplification of the Upstream Region Containing the "−10" Sequence of the Ppur by PCR Based on the information from GenBank (Accession No. NC_000964), PCR primer of SEQ ID NO: 42 and each of the primers (SEQ ID NO: 23-25) containing three kinds of the modified Ppur sequence were designed:

AATAGATATAAAGAGGTGAGTCTGC (SEQ ID NO: 42)

<for Ppur1 Modification>
TTTTGATTTCATGTTTattataACAACGGACATGGATA (SEQ ID NO: 23; the nucleotide sequence indicated by lower-case letters is the Ppur1 sequence)

<for Ppur3 Modification>
TTTTGATTTCATGTTTatcataACAACGGACATGGATA (SEQ ID NO: 24; the nucleotide sequence indicated by lower-case letters is the Ppur3 sequence)

<for Ppur5 Modification>
TTTTGATTTCATGTTTattttaACAACGGACATGGATA (SEQ ID NO: 25; the nucleotide sequence indicated by lower-case letters is the Ppur5 sequence).

PCR was conducted (94° C., 30 seconds; 55° C., 1 minute; 72° C., 1 minute; 30 cycles; Gene Amp PCR System Model 9600 (made by Perkins Elmer)) using the above-described primers and a template of a chromosomal DNA of B. Subtilis 168 Marburg strain, to amplify three kinds of fragments of about 1,060 bp containing Ppur and its upstream sequence.

(ii) Amplification of the Downstream Region Containing the Modified "−10" Sequence of Ppur by PCR Based on the information from GenBank (Accession No. NC_000964), PCR primer of SEQ ID NO: 26 and each of the primers containing the three kinds of modified Ppur sequences were prepared:

GGGTAATAAGCAGCAGCTCACTTCC (SEQ ID NO: 26)

<for Ppur1 Modification>
TATCCATGTCCGTTGTtataatAAACATGAAATCAAAA (SEQ ID NO: 27; the nucleotide sequence indicated by lower-case letters is the Ppur 1 sequence, this primer is complementary to SEQ ID NO: 23)

<for Pur3 Modification>
TATCCATGTCCGTTGTtatgatAAACATGAAATCAAAA (SEQ ID NO: 28; the nucleotide sequence indicated by lower-case letters is the Ppur 3 sequence, this primer is complementary to SEQ ID NO: 24)

<for Pur5 Modification>
TATCCATGTCCGTTGTtaaaatAAACATGAAATCAAAA (SEQ ID NO: 29: the nucleotide sequence indicated by lower-case letters is the Ppur 5 sequence, this primer is complementary to SEQ ID NO: 25)

PCR was conducted (94° C., 30 seconds; 55° C., 1 minute; 72° C., 1 minute; 30 cycles; Gene Amp PCR System Model 9600 (made by Perkins Elmer)) using the above-described primers and a template of a chromosomal DNA of B. Subtilis 168 Marburg strain, to amplify three kinds of fragments of about 1,070 bp containing the Ppur "−10" sequence and its downstream sequence.

(iii) Amplification of the Ppur Region Containing the Modified "−10" Sequence by PCR PCR was conducted (94° C., 30 seconds; 55° C., 1 minute; 72° C., 2 minute; 30 cycles; Gene Amp PCR System Model 9600 (made by Perkins Elmer)) using primers of SEQ ID NOS: 42 and 26 and a template of each of the DNA fragments amplified in the above (i) and (ii) and purified on a MicroSpin Column S-400 (Amersham Pharmacia Biotech), to amplify fragments of the Ppur region in which the "−10" sequence had been replaced with Ppur1, Ppur3, and Ppur5, respectively.

(iv) Preparation of a Bacterial Strain in Which the "−10" Sequence is Replaced by Each of Ppur1, Ppur3, and Ppur5

DNA fragments of the Ppur region containing the modified "−10" sequence (Ppur1, Ppur3, or Ppur5) obtained in the above (iii) were subjected to agarose gel electrophoresis and the target fragments were extracted from the gel. Competent cells of strain KMBS 198 prepared as described above were transformed with the obtained DNA fragments, and colonies that were capable of growing on minimal medium agar plate were selected. Chromosomal DNA was prepared from these colonies and the strains in which the Ppur::cat region on the chromosome had been replaced by Ppur1, Ppur3, and Ppur5 by double-crossover recombination were identified by the PCR as described in the above (iii). The recombinants thus obtained were not auxotrophic for adenine. The obtained strains were named KMBS210, KMBS211, and KMBS222, respectively.

(3) Preparation of a Strain in Which an Attenuator Sequence of the Purine Operon is Deleted A bacterial strain in which the attenuator sequence located downstream of Ppur was deleted was prepared from Bacillus subtilis (B. subtilis 168 Marburg strain; ATCC6051) as follows. FIG. 1 shows the sequence that was deleted.

(i) Amplification of the Partially Deleted Attenuator Sequence and its Upstream Region by PCR Based on the information from GenBank (Accession No. NC_000964), PCR primer of SEQ ID NO: 17 and the primer of SEQ ID NO: 30 having the following nucleotide sequence were prepared:

GCTTTTGTTTTCAGAAAATAAAAAATAcgATATATCCATGTCAGTTTTATCG (SEQ ID NO: 30, the nucleotide sequence indicated by lower-case letters is a junction created by deleting a portion (75 bp) of the attenuator sequence).

PCR was conducted (94° C., 30 seconds; 53° C., 1 minute; 72° C., 1 minute; 30 cycles; Gene Amp PCR System Model 9600 (made by Perkins Elmer)) using the above-described primers and a template of a chromosomal DNA of B. subtilis 168 Marburg strain to amplify a fragment containing a partially deleted attenuator sequence and its upstream sequence (about 840 bp).

(ii) Amplification of the Partially Deleted Attenuator Sequence and its Downstream Region by PCR Based on the information from GenBank (Accession No. NC_000964), PCR primer of SEQ ID NO: 26 and the primer of SEQ ID NO: 31 having the following nucleotide sequence were prepared:

CGATAAAACTGACATGGATATATcgTATTTTTTATTTTCTGAAAACAAAAGC (SEQ ID NO: 31; the nucleotide sequence indicated by lower-case letters is a junction created by deleting a part (75 bp) of the attenuator sequence. This primer is complementary to SEQ ID NO: 30).

PCR was conducted (94° C., 30 seconds; 53° C., 1 minute; 72° C., 1 minute; 30 cycles; Gene Amp PCR System Model 9600 (Perkins Elmer)) using the above-described primers and a template of a chromosomal DNA of B. subtilis 168 Marburg strain to amplify a fragment containing a partially deleted attenuator sequence and its downstream sequence (about 850 bp).

(iii) Amplification of a Ppur Region Containing a Partially Deleted Attenuator Sequence by PCR The DNA fragments amplified in the above (i) and (ii) were purified on a MicroSpin Column S-400 (Amersham Pharmacia Biotech), and a suitable quantity of the mixture was used as template, and primers of SEQ ID NOS: 17 and 26 were used, and PCR (94° C., 30 seconds; 53° C., 1 minute; 72° C., 2 minutes; 30 cycles; Gene Amp PCR System Model 9600 (Perkins Elmer)) was conducted, to amplify a fragment of the Ppur region containing a partially deleted attenuator sequence.

(iv) Construction of a Bacterial Strain with a Partially Deleted Attenuator Sequence The DNA fragment of the Ppur region (Ppur-Δatt) containing the partially deleted attenuator sequence obtained in the above (iii) was subjected to agarose gel electrophoresis and the target fragment was extracted from the gel. Competent cells of the strain KMBS198 prepared as described above were transformed with the DNA the obtained fragment, and the colonies that were capable of growing on a minimal medium agar plate were selected. Chromosomal DNA was prepared from these colonies and the strain in which the Ppur::cat region on the chromosome had been substituted with Ppur-Δatt by double-crossover recombination was identified by the PCR as described in the above (iii). The obtained strain was auxotroph for adenine. The strain was named KMBS252.

(4) A bacterial strain derived from *Bacillus subtilis* (*B. subtilis* strain 168 Marburg; ATCC6051) that was modified by changing the "−10" sequence of Ppur to the consensus sequence TATAAT (Ppur1) and partially deleting the attenuator sequence was prepared as follows.

(i) Amplification of the Upstream Region Containing the Modified "−10" Sequence (Ppur1) of Ppur by PCR PCR was conducted (94° C., 30 seconds; 55° C., 1 minute; 72° C., 1 minute; 30 cycles; Gene Amp PCR System Model 9600 (Perkins Elmer)) using the primers of SEQ ID NOS: 42 and 23 designed based on GenBank Accession No. NC_000964 and a template of the chromosomal DNA of a bacterial strain in which the attenuator sequence had been partially deleted such as the KMBS252 strain prepared in the above (3), to amplify a fragment of about 1060 comprising the upstream region of Ppur containing Ppur1.

(ii) Amplification of a Fragment Containing Ppur1, a Partially Deleted Attenuator Region, and its Downstream Region by PCR PCR was conducted (94° C., 30 seconds; 55° C., 1 minute; 72° C., 1 minute; 30 cycles; Gene Amp PCR System Model 9600 (made by Perkins Elmer)) using the primers of SEQ ID NOS: 26 and 27 designed based on GenBank Accession No. NC_000964 and a template of the chromosomal DNA of a bacterial strain in which the attenuator sequence had been partially deleted such as the KMBS252 strain prepared in the above (3), to amplify a fragment of about 990 bp containing Ppur1, a partially deleted attenuator region, and the downstream region.

(iii) Amplification of a Fragment Containing the Ppur Region Containing Ppur1 and a Partially Deleted Attenuator Region by PCR The DNA fragments amplified in the above (i) and (ii) were purified on a MicroSpin Column S-400 (Amersham Pharmacia Biotech), and a suitable quantity of the mixture was used as template, and primers of SEQ ID NOS: 42 and 26 were used, and PCR (94° C., 30 seconds; 55° C., 2 minute; 72° C., 2 minute; 30 cycles; Gene Amp PCR System Model 9600 (made by Perkins Elmer)) was conducted, to amplify a fragment of the Ppur region containing Ppur1 and a partially deleted attenuator sequence.

(iv) Preparation of a Bacterial Strain in which the "−10" Sequence was Changed to Ppur1 and the Attenuator Sequence was Partially Deleted The DNA fragment of the Ppur region (Ppur1-Δatt) containing Ppur1 and a partially deleted attenuator sequence obtained in the above (iii) was subjected to agarose gel electrophoresis and the target fragment was extracted from the gel. Competent cells of strain KMBS198 prepared as described above were transformed with the obtained DNA fragment, and the colonies that were capable of growing on minimal medium agar plate were selected. Chromosomal DNA was prepared from these colonies and the strains in which the Ppur::cat region on the chromosome had been substituted with Ppur1-Δatt by double-crossover recombination were identified by PCR as described in the above (iii). The obtained recombinant strain was not auxotrophic for adenine. The strain was named KMBS261.

(5) Construction of a Plasmid for Measuring Transcription Activity of Purine Operon Based on the information from GenBank (Accession No. NC_000964), PCR primers having the following nucleotide sequences were prepared:

cgcaagcttTATTTTCTGAAAACAAAAGC (SEQ ID NO: 32; the nucleotide sequence indicated by lower-case letters is a tag containing a HindIII site);

cgcggatccTTTCTCTTCTCTCATCCAGC (SEQ ID NO: 33: the nucleotide sequence indicated by lower-case letters is a tag containing a BamHI Site).

PCR was conducted (94° C., 30 seconds; 55° C., 1 minute; 72° C., 2 minutes; 30 cycles; Gene Amp PCR System Model 9600 (made by Perkins Elmer)) using the above-described primers and a template of a chromosomal DNA of *B. subtilis* 168 Marburg strain to amplify a fragment containing a part of the purE structural gene (445 bp) and its upstream region (40 bp) containing an SD sequence.

The amplified fragment was purified with a MinElute PCR Purification Kit (Qiagen) and digested with restriction enzymes at HindIII and BamHI. The DNA fragment was inserted using T4 DNA ligase into the upstream region of lacZ in pMutin4 (Vagner, V., et al., Microbiology, 1998, 144, 3097-3104) that had been treated with the same enzymes, and thereby a plasmid pKM191 was obtained. pKM191 contains a part of the purE structural gene (445 bp) and its upstream region (40 bp) containing an SD sequence.

(6) Preparation of a Bacterial Strain for Measuring the Transcription Activity of Purine Operon A bacterial strain for measurement of transcription activity of purine operon was constructed as follows.

(i) Preparation of a Bacterial Strain in Which Ppur is Disrupted

Chromosomal DNA was prepared from KMBS198 (Ppur-::cat), and used to transform competent cells of KMBS4 strain (JP2004-242610A) which has a disrupted-type of purR (purR::spc) prepared as described above, and the colonies that were capable of growing on LB agar plate containing 2.5 μg/mL of chloramphenicol were selected. The obtained recombinant strain was purR-deficient and auxotrophic for adenine. The strain was named KMBS278.

(ii) Construction of a Bacterial Strain having a purR-Deletion and the Modified Ppur Region The chromosomal DNA was prepared from the strains KMBS210, KMBS211, KMBS222, KMBS252, and KMBS261, respectively. This DNA was used to transform competent cells of strain KMBS278 prepared as described above, and the colonies that were capable of growing on a minimal medium agar plate and exhibit spectinomycin-resistance were selected by using LB agar plate. Chromosomal DNA was prepared from these colonies and the strains in which the Ppur::cat region on the chromosome had been substituted with a modified Ppur region by double-crossover recombination were identified by PCR as described in the above (1)(iv). The obtained recombinant strains were not auxotrophic for adenine. The strains were named KMBS283, KMBS284, KMBS285, KMBS286, and KMBS287, respectively.

(iii) Preparation of a Bacterial Strain in Which pKM191 is Introduced

Competent cells of each of B. subtilis 168 Marburg strain, KMBS4, KMBS283, KMBS284, KMBS285, KMBS286, and KMBS287 prepared as described above were transformed with plasmid pKM191 for measurement of transcription activity of purine operon, and colonies that were capable of growing on LB agar plate containing 2.5 µg/mL of chloramphenicol were selected. The obtained colonies were single crossover recombinants, in which native purE gene was recombined with purE gene of pKM191 containing lacZ gene by homologous recombination, and turned blue on LB agar plate containing 80 µg/mL of X-Gal when lacZ gene is expressed by Ppur. The strains were named KMBS292, KMBS295, KMBS296, KMBS297, KMBS298, KMBS299, and KMBS300, respectively.

(7) Measurement of Transcription Activity of Purine Operon

Ppur transcription activity was measured based on lacZ by using the bacterial strains prepared in the above (6) (iii). The KMBS292 strain having gene structure of 168 Marburg and the KMBS295 strain having gene structure of a purine operon repressor purR gene-disrupted were used as control strains. The other strains had purR gene-disrupted background, and among them, the strains KMBS296, KMBS297, and KMBS298 have the modified "−10" sequences, and the KMBS299 strain has a partially deleted attenuator sequence, and the KMBS300 strain has both the modified "−10" sequence (Ppur1) and a partially deleted attenuator sequence.

These six strains were cultured in LB medium (20 mL) containing guanine (20 mg/L) at 37° C. until the late log growth phase ($OD_{600}$=1.1 to 1.4). A suitable quantity of the culture solution was sampled and β-galactosidase activity therein was measured. The β-galactosidase activity was measured by the method of Fouet et al. (Fouet, A. and Sonenshein, A. L., J. Bacteriol., 1990, 172, 835-844). The results are shown in FIG. 2. (WT shows the activity of KMBS296, ΔRpurR shows the activity of KMBS295, ΔR+Ppur1 shows the activity of KMBS296, ΔR+Ppur3 shows the activity of KMBS297, ΔR+Ppur5 shows the activity of KMBS298, ΔR+Ppur-Δatt shows the activity of KMBS299, andΔR+Ppur1-Δatt the activity of KMBS300. The activity in the ΔpurR strain increased to 4.5-fold as compared to the 168 Marburg strain. Furthermore, modification of the "−10" sequence to Ppur1 increased the activity about 3-fold. Partial deletion of the attenuator sequence resulted in about 15-fold increase in the activity, and in the strain having both of the mutations, the activity increased to 26.5-fold.

Example 4

<Construction and Evaluation of Strains in Which the Modified Ppur Region is Introduced>

(1) The modified purine operon promoter and the partially deleted attenuator sequence were introduced into a recombinant YMBS2 strain that is derived from Bacillus subtilis (B. subtilis 168 Marburg strain; ATCC6051) and in which the purine operon repressor gene (purR), succinyl AMP synthase gene (purA), and purine nucleoside phosphorylase gene (pupG) had been disrupted and a guanine-auxotrophic leaky mutation (guaB(A1) mutation) had been introduced into the IMP dehydrogenase gene.

A chromosomal DNA was prepared from B. subtilis 168 Marburg strain, and used to transform the competent cells of KMBS113 strain (purR::spc purA::erm ΔpupG trpC2) prepared as described above, and the colonies that were capable of growing on minimal medium agar plate (that is, not auxotrophic for adenine) and exhibited spectinomycin-resistance were selected by using LB agar plate. Chromosomal DNA was prepared from these colonies, and among them, ΔpupG strain was identified by PCR as in the Example 1 (1)(iv). The obtained strain was named KMBS180 (purR:: spc ΔpupG trpC2).

Next, a chromosomal DNA of strain KMBS198 was prepared and used to transform competent cells of strain KMBS 180 prepared as described above, and the colonies that were capable of growing on an LB agar plate containing 2.5 µg/mL of chloramphenicol were selected. Chromosomal DNA was prepared from these colonies, and among them, the strain in which the Ppur region on the chromosome had been substituted with Ppur::cat by double-crossover recombination was identified by PCR in the same way as in Example 3(1)(iv). The strain was auxotrophic for adenine; the strain was named KMBS216 (Ppur::cat purR::spc ΔpupG trpC2).

Chromosomal DNA of KMBS252 (Ppur-Δatt) was prepared and used to transform competent cells of strain KMBS216 prepared as described above, and the colonies that were capable of growing on a minimal medium agar plate were selected. Chromosomal DNA was prepared from these colonies, and among them, the bacterial strain in which the Ppur::cat on the chromosome had been substituted with the Ppur-Δatt region by double-crossover recombination was identified by PCR in the same way as in Example 3(1)(iv). The bacterial strain was not auxotrophic for adenine; the strain was named KMBS264 (Ppur-Δatt purR:: spc ΔpupG trpC2). KMBS261, which is a bacterial strain in which Ppur1-Δatt is introduced, was obtained by the same procedure.

Chromosomal DNA of KMBS9 (purA::erm trpC2; US2004-0166575) was prepared and used to transform competent cells of strains KMBS264 and KMBS261 prepared as described above, and the colonies that were capable of growing on LB agar plate containing 0.5 µg/mL of erythromycin were selected. These strains were not auxotrophic for adenine; and the strains were named KMBS265 (Ppur-Δatt purR::spc purA::erm ΔpupG trpC2) and KMBS267 (Ppur1-Δatt purR::spc purA::erm ΔpupG trpC2), respectively.

Next, chromosomal DNA of KMBS193 (guaB::kan) was prepared and used to transform competent cells of strains KMBS265 and KMBS267 prepared as described above, and the colonies that were capable of growing on LB agar plate containing 2.5 µg/mL of kanamycin and 20 µg/mL of guanine were selected. These strains were auxotrophic for guanine; and these strains were named KMBS270 (Ppur-Δatt purR::spc purA::erm guaB::kan ΔpupG trpC2) and KMBS271 (Ppur1-Δatt purR::spc purA::erm guaB::kan ΔpupG trpC2), respectively.

Finally, chromosomal DNA of YMBS2 (guaB(A1)) was prepared and used to transform competent cells of strains KMBS270 and KMBS271 prepared as described above, and the colonies that were capable of growing on minimal medium agar plate containing 20 µg/mL of adenine were selected. These strains were auxotrophic for guanine; and these strains were named KMBS279 (Ppur-Δatt purR::spc purA::erm guaB(A1) ΔpupG trpC2) and KMBS280 (Ppur1-Δatt purR::spc purA::erm guaB::(A1) ΔpupG trpC2), respectively.

(2) Purine Nucleoside Production by Bacterial Strains having the Modified Ppur Region Bacterial strains having the modified Ppur region (strains KMBS279 and KMBS280) and a control YMBS2 strain were uniformly spread over PS plate medium (30 g/L of soluble starch, 5 g/L of yeast extract, 5 g/L of polypeptone, 20 g/L of agar, adjusted to pH 7.0 with KOH) and cultured overnight at 34° C. One-eighth of the bacteria cells on the plate were inoculated into 20 mL of fermentation medium in a 500 mL capacity Sakaguchi flask. Subsequently, 50 g/L of calcium carbonate was added and the bacteria were cultured at 34° C. with shaking. Sampling was conducted at the time point of 96 hour after the start of culturing, and the amounts of inosine and hydroxanthine in the culture medium were measured by conventional methods.

Composition of fermentation medium:

| | |
|---|---|
| Glucose | 60 g/L |
| KH$_2$PO$_4$ | 1 g/L |
| NH$_4$Cl | 32 g/L |
| Mameno (T-N)* | 1.35 g/L |
| DL-methionine | 0.3 g/L |
| L-tryptophan | 0.02 g/L |
| Adenine | 0.1 g/L |
| Guanine | 0.05 g/L |
| MgSO$_4$ | 0.4 g/L |
| FeSO$_4$ | 0.01 g/L |
| MnSO$_4$ | 0.01 g/L |
| GD113 | 0.01 mL/L |
| (adjusted to pH 7.0 with KOH) | |
| Calcium carbonate | 50 g/L |

*Protein hydrolysis product

TABLE 3

| B. subtilis strain | OD562 | Inosine, g/L | Hypoxanthine, g/L |
|---|---|---|---|
| YMBS2 | 6.5 | 3.08 | 0.32 |
|  | 6.5 | 3.15 | 0.25 |
| KMBS279 | 4.9 | 3.99 | 0.43 |
|  | 5.5 | 4.57 | 0.36 |
| KMBS280 | 5.7 | 5.31 | 0.39 |
|  | 5.7 | 5.26 | 0.39 |

Example 5

<Construction of a Bacterium with Enhanced PRPP Synthetase Activity>

(1) The SD sequence of PRPP synthetase gene (prs) was modified in the recombinant KMBS280 strain which is derived from *Bacillus subtilis* (*B. subtilis* 168 Marburg strain; ATCC6051) and in which the purine operon repressor gene (purR), succinyl-AMP synthase gene (purA) and purine nucleoside phosphorylase gene (pupG) had been disrupted, and a guaB (A1) mutation had been introduced into the IMP hydrogenase gene (guaB); and which has the modified purine operon promoter region.

(i) Amplification of Upstream Region of the SD Sequence Containing a Modified SD Sequence by PCR Based on the information from GenBank (Accession No. NC_000964), PCR primer of SEQ ID NO: 34 and the primers having the modified Ppur sequence were designed:

cgcggatccAACATACACAAAGAGAAGCGAAAGC (SEQ ID NO: 34; the nucleotide sequence indicated by lower-case letters is a tag containing a BamHI site);

<for Modification SD1>
GATTAGACATGGATAAACCTCCttATT-TAGGATTATTTTTTATGAA (SEQ ID NO: 35; the nucleotides indicated by lower-case letters is a mutation point, and the sequence in the box is a modified SD sequence 1);

<for Modification SD2>
GATTAGACATGGATAAACCTCCtAATT-TAGGATTATTTTTTATGAA (SEQ ID NO: 36; the nucleotide indicated by lower-case letter is a mutation point, and the sequence in the box is a modified SD sequence 2);

<for Modification SD3>
GATTAGACATGGATAAACCTCCGtATT-TAGGATTATTTTTTATGAA (SEQ ID NO: 37; the nucleotide indicated by lower-case letter is a mutation point, and the sequence in the box is a modified SD sequence 3).

PCR was conducted (94° C., 30 seconds; 55° C., 1 minute; 72° C., 1.5 minute; 30 cycles; Gene Amp PCR System Model 9600 (Perkins Elmer)) using the above-described primers and a template of the chromosomal DNA of *B. subtilis* 168 Marburg strain, to amplify a fragment containing a region upstream of the prs start codon (about 1,040 bp) and its downstream sequence (10 bp).

(ii) Amplification of a Region Downstream of the SD Sequence Containing a Modified SD Sequence by PCR Based on the information from GenBank (Accession No. NC_000964), PCR primer of SEQ ID NO: 38 and the three kinds of primers having modified SD sequence were prepared.

cgcggatccGGTTTAGCTGAACAGAT-AGCTGACTGATTGC (SEQ ID NO: 38; the nucleotide sequence indicted by lower-case letters is a tag containing a BamHI site);

<for SD1 Modification>
TTCATAAAAAATAATCCTAAATaaGGAG-GTTTATCCATGTCTAATC (SEQ ID NO: 39: the nucleotides indicated by lower-case letters are a mutation point; the sequence in the box is SD sequence 1; this primer is complementary to SEQ ID NO: 35)

<for SD2 Modification>
TTCATAAAAAATAATCCTAAATTaGGAG-GTTTATCCATGTCTAATC (SEQ ID NO: 40: the nucleotide indicated by lower-case letter is a mutation point; the sequence in the box is SD sequence 2; this primer is complementary to SEQ ID NO: 36)

<for SD3 Modification>
TTCATAAAAAATAATCCTAAATaCGGAG-GTTTATCCATGTCTAATC (SEQ ID NO: 41: the nucleotide indicated by lower-case letter is a mutation point; the sequence in the box is SD sequence 3; this primer is complementary to SEQ ID NO: 37)

PCR was conducted (94° C., 30 seconds; 55° C., 1 minute; 72° C., 1.5 minute; 30 cycles; Gene Amp PCR System Model 9600 (Perkins Elmer)) using the above-described primers and a template of the chromosomal DNA of *B. subtilis* 168 Marburg strain, to amplify a fragment containing a region upstream of prs start codon (36 bp) and the following downstream sequence (about 960 bp).

(iii) Amplification of a Region Containing the Modified SD Sequence by PCR

PCR was conducted (94° C., 30 seconds; 55° C., 1 minute; 72° C., 2.5 minutes; 30 cycles; Gene Amp PCR System Model 9600 (Perkins Elmer)) using primers of SEQ ID NOS: 34 and 38 and a template of a suitable mixture of the amplified DNA fragments of the above (i) and (ii) after purification on a MicroSpin Column S-400 (Amersham Pharmacia Biotech), to amplify a fragment in which the SD sequence was modified to be SD sequence 1, 2, or 3, respectively (SD1, SD2, SD3).

(iv) Cloning of a Region Containing the Modified SD Sequence

The DNA fragment having a region containing the modified SD sequence (SD1, SD2, SD3) was purified and digested with BamHI, and ligated by using T4 DNA ligase to a recombination vector pJPM1 (Mueller et al., J. Bacteriol., 1992, 174, 4361-4373) that had been digested with the same enzyme and dephosphorylated with calf intestinal phosphatase, and thereby, the plasmids pKM196 (SD1), pKM197 (SD2), and pKM198 (SD3) were obtained.

(v) Preparation of an Inosine-Producing Bacterial Strain in Which the Modified SD Sequence is Introduced The plasmids pKM196 (SD1), pKM197 (SD2), and pKM198 (SD3) were used to transform competent cells of the strain KMBS280 prepared as described above, and the colonies that were capable of growing on an LB agar plate containing 2.5 μg/mL of chloramphenicol (single-crossover recombinant) were selected.

The obtained single-crossover recombinants were inoculated on 10 mL of LB medium and successively subcultured for several days at 37° C. The colonies exhibiting chloramphenicol-sensitivity was selected on LB agar medium. Chromosomal DNA was prepared from the chloramphenicol-sensitive colonies. PCR was conducted in the same manner as described above using primers of SEQ ID NOS: 34 and 38. The DNA sequence was analyzed to identify bacterial strains in which the SD sequence of the prs gene on the chromosome had been replaced with the modified SD sequences by the double-crossover recombination. Each type of the double-crossover recombinants thus obtained was named: KMBS310 (SD1), KMBS318 (SDS), KMBS322 (SD3).

(2) Purine Nucleoside Production by Inosine-Producing Bacterial Strains in Which the Modified SD Sequence is Introduced Inosine-producing bacterial strains (strains KMBS310, KMBS318, and KMBS322) having the modified SD sequences SD1, SD2, or SD3, and a control KMBS280 strain were uniformly spread over a PS medium plate (soluble starch 30 g/L, yeast extract 5 g/L, polypeptone 5 g/L, agar 20 g/L, adjusted to pH 7.0 with KOH) and cultured overnight at 34° C. One-eighth of the bacterial cells on the plate were inoculated on 20 mL of fermentation medium in a 500 mL capacity Sakaguchi flask. Subsequently, calcium carbonate was added at 50 g/L and the bacteria were cultured at 34° C. with shaking. Sampling was conducted 120 hours after the start of culturing, and the amounts of inosine and hypoxanthine in the culture medium were measured by conventional methods.

| Glucose | 60 g/L |
| KH$_2$PO$_4$ | 1 g/L |
| NH$_4$Cl | 32 g/L |
| Mameno (T-N)* | 1.35 g/L |
| DL-methionine | 0.3 g/L |
| L-tryptophan | 0.02 g/L |
| Adenine | 0.1 g/L |
| Guanosine | 0.075 g/L |
| MgSO$_4$ | 0.4 g/L |
| FeSO$_4$ | 0.01 g/L |
| MnSO$_4$ | 0.01 g/L |
| GD113 | 0.01 mL/L |
| (adjusted to pH 7.0 with KOH) | |
| Calcium carbonate | 50 g/L |

*Protein hydrolysis product

TABLE 4

| B. subtilis strain | OD562 | Inosine (g/L) | Hypoxanthine (g/L) |
|---|---|---|---|
| KMBS280 | 4.2 | 3.76 | 0.45 |
|  | 4.2 | 3.70 | 0.47 |
| KMBS310 | 4.4 | 4.88 | 0.55 |
|  | 4.4 | 5.07 | 0.53 |
| KMBS318 | 4.4 | 4.41 | 0.43 |
|  | 4.4 | 4.58 | 0.43 |
| KMBS322 | 4.4 | 3.85 | 0.40 |
|  | 4.7 | 4.45 | 0.40 |

Example 6

Construction of bacterial strains having enhanced activity of an enzyme involved in oxidative pentosephosphate pathway (1) Construction of a Strain having Enhanced Glucose-6-Phosphate Dehydrogenase Activity A plasmid carrying a zwf gene that encodes glucose-6-phosphate dehydrogenase was introduced into a recombinant strain which is derived from Bacillus subtilis (B. subtilis 168 Marburg strain; ATCC6051) and in which purine operon repressor gene (purR), succinyl-AMP synthase gene (purA), and purine nucleoside phosphorylase genes (pupG and deoD) had been disrupted; a guaB (A1) mutation had been introduced into IMP dehydrogenase gene; and which has the modified purine operon promoter region and the modified SD sequence in PRPP synthetase gene (prs).

(i) Amplification of the Structural Gene and Upstream Region of the zwf Gene by PCR Based on the information from GenBank (Accession No. NC_000964 CAB14317. glucose-6-phospha . . . [gi: 2634820]), PCR primers having the nucleotide sequences shown below were prepared:

cgcggatccGCCTCTGAAAAGAACAATCC (SEQ ID NO: 43; the nucleotide sequence indicated by lower-case letters is a tag containing a BamHI site);

cgcggatccAAGCTCTTAAGCTTTGGGGG (SEQ ID NO: 44; the nucleotide sequence indicated by lower-case letters is a tag containing a BamHI site).

PCR was conducted (94° C., 30 seconds; 55° C., 1 minute; 72° C., 2 minutes; 30 cycles; Gene Amp PCR System Model 9600 (made by Perkins Elmer)) using the above-described primers and a template of a chromosomal DNA of the B. subtilis 168 Marburg strain, to amplify a fragment containing the structural gene and upstream region (about 160 bp) of the zwf gene.

(ii) Cloning of the Structural Gene and Upstream Region of the zwf Gene

The DNA fragment containing the structural gene and its upstream region of the zwf gene was purified and then digested with BamHI, and ligated by using T4 DNA ligase to an E. coli-Bacillus shuttle vector pHY300PLK (made by Yakult Corp.) that had been digested with the same enzyme and dephosphorylated with calf intestinal phosphatase, and thereby, a plasmid containing the zwf gene was obtained.

(iii) Construction of an Inosine-Producing Bacterial Strain in Which a Plasmid Containing the zwf Gene is Introduced The obtained plasmid or control pHY300PLK vector was used to transform competent cells of the inosine-producing strain KMBS321, and the colonies that were capable of growing on LB agar plate containing 12.5 μg/mL of tetracycline were selected. The strain introduced with the plasmid carrying the zwf gene was named TABS125 and the strain introduced with pHY300PLK was named TABS100.

The KMBS321 strain was constructed as follows.

Genomic DNA was isolated from the deoD-deficient mutant strain KMBS16 (purR::spc purA::erm deoD::kan: US2004-0166575A) by the method of Fouet and Sonenshein (J. Bacteriol., 1990, 172, 835-844) and the genomic DNA was used to transform competent cells of B. subtilis 168 Marburg, prepared by the method of Dubunau and Davidoff-Abelson to obtain colonies which were capable of growing on an LB agar plate containing 5 μg/ml of kanamycin. Among the colonies which appeared, colonies which were not resistant to spectinomycin or erythromycin were selected, and one of such colonies was named KMBS (deoD::kan).

Genomic DNA was isolated from the KMBS(deoD::kan) by the method of Fouet and Sonenshein and the genomic DNA was used to transform competent cells of the KMBS310 as mentioned above to obtain colonies which were capable of growing on an LB agar plate containing 20 μg/ml of guanine. Among the colonies which appeared, a strain in which a wild-type deoD gene was replaced by deoD::kan and the other mutations derived from KMBS310 did not revert to the respective wild-type genes was selected, and the strain was named KMBS321.

An increase in glucose-6-phosphate dehydrogenase activity was confirmed as follows.

<Method of Measuring Glucose-6-Phosphatedehydrogenase (Product of the zwf Gene) Activity>
Reaction solution
50 mM Tris-HCl (pH7.6)
10 mM MgSO$_4$.7H$_2$O
0.3 mM NADP
4 mM glucose 6-phosphate
Enzyme solution The above-described reaction solution (1 mL) was prepared and the reaction was performed at 37° C. The change in concentration of the NADPH was measured based on absorption at 340 nm.

(iv) The Purine-Derived Nucleic Acid Production by the Inosine-Producing Strains in Which the Plasmid Containing the zwf Gene is Introduced The TABS125 strain and TABS100 strain were uniformly spread over a PS plate medium (soluble starch 30 g/L, yeast extract 5 g/L, polypeptone 5 g/L, agar 20 g/L, adjusted to pH 7.0 with KOH) containing 12.5 μg/mL of tetracycline and cultured at 34° C. overnight. One-eighth of the bacterial cells on the plate were inoculated into 20 mL of fermentation medium in a 500 mL capacity Sakaguchi flask. Subsequently, calcium carbonate was added at 50 g/L and the bacteria were cultured at 34° C. with shaking. Sampling was conducted at 120 hours after the start of culturing, and the amounts of inosine and hypoxanthine in the culture medium were measured by conventional methods (Table 5). It was confirmed that a bacterial strain with enhanced purine nucleoside-producing ability was obtained.

Composition of fermentation medium:

| | |
|---|---|
| Glucose | 60 g/L |
| KH$_2$PO$_4$ | 1 g/L |
| NH$_4$Cl | 32 g/L |
| Mameno (T-N)* | 1.35 g/L |
| Yeast extract | 1 g/L |
| DL-methionine | 0.3 g/L |
| L-tryptophan | 0.02 g/L |
| Adenine | 0.1 g/L |
| Guanosine | 0.075 g/L |
| MgSO$_4$ | 0.4 g/L |
| FeSO$_4$ | 0.01 g/L |
| MnSO$_4$ | 0.01 g/L |
| GD113 | 0.01 mL/L |
| (adjusted to pH 7.0 with KOH) | |
| Calcium carbonate | 50 g/L |

*Protein hydrolysis product

TABLE 5

| B. subtilis strain | OD610 | Inosine (%)*[1] |
|---|---|---|
| TABS100 | 8.4 | 18.73 |
| | 8.7 | 19.24 |
| TABS125 | 9.1 | 21.64 |
| | 9.0 | 21.99 |

*[1]Ratio of the produced inosine to the amount of the consumed glucose (g/g)

(2) Construction of a Strain with Enhanced Ribose-5-Phosphate Isomerase Activity Expression of a gene encoding ribose-5-phosphate isomerase (ywlF gene) was enhanced in a recombinant strain which is derived from Bacillus subtilis (B. subtilis 168 Marburg strain; ATCC6051) and in which purine operon repressor gene (purR), succinyl-AMP synthase gene (purA), and purine nucleoside phosphorylase gene (pupG and deoD) had been disrupted; the guaB (A1) mutation had been introduced into IMP dehydrogenase gene; and which has the modified purine operon promoter region and the modified SD sequence in PRPP synthetase gene (prs).

(i) Amplification of the Structural Gene and Upstream Region of the ywlF Gene by PCR Based on the information from GenBank (Accession No. NC_000964 CAB15709 [gi:2636217]), PCR primers having the nucleotide sequences shown were prepared:

cgcgaattcGTAGATAAGTTGTCAGAAAATCTGC (SEQ ID NO: 45; the nucleotide sequence indicated by lower-case letters is a tag containing an EcoRI site);

cgcgaattcTGTTTCAACTCATTCATTAAACAGC (SEQ ID NO: 46; the nucleotide sequence indicated by lower-case letters is a tag containing an EcoRI site).

PCR was conducted (94° C., 30 seconds; 55° C., 1 minute; 72° C., 1 minute; 30 cycles; Gene Amp PCR System Model 9600 (made by Perkins Elmer)) using the above-described primers and a template of a chromosomal DNA of the B. subtilis 168 Marburg strain, to amplify a fragment containing the structural gene and upstream region (about 160 bp) of the ywlF gene.

(ii) Cloning of the Structural Gene and Upstream Region of the ywlF Gene

The DNA fragment containing the structural gene and its upstream region of the ywlF gene was purified and then digested with EcoRI and ligated by using T4 DNA ligase to the E. coli-Bacillus shuttle vector pHY300PLK (made by Yakult Corp.) that had been digested with the same enzyme and dephosphorylated with calf intestinal phosphatase, and thereby a plasmid for enhancing expression of the ywlF gene was obtained.

(iii) Preparation of an Inosine-Producing Bacterial Strain in Which the Plasmid Containing rge ywlF Gene is Introduced The obtained plasmid or pHY300PLK vector was used to transform the competent cells of the inosine-producing bacterial strains KMBS321 prepared as described above, and the colonies that were capable of growing on an LB agar plate containing 12.5 µg/mL of tetracycline were selected. The strain in which the plasmid carrying ywlF was introduced was named TABS102.

An increase in ribose-5-phosphate isomerase activity was confirmed as follows.

<Method of Detecting Ribose-5-Phosphate Isomerase (ywlF Gene Product) Activity>
Reaction solution
50 mM HEPES (pH 7.5)
0.1 M NaCl
10 mM Ribose-5-phosphate
Enzyme solution The above reaction solution (mL) was prepared and the reaction was initiated at 37° C. The change in concentration of riboluse-5-phosphate was measure based on absorption of 290 nm.

(iv) The Production of Purine-Derived Nucleic Acids by the Inosine-Producing Bacterial Strain Introduced with the Plasmid Carrying the ywlF Gene The TABS102 strain and TABS100 strain were introduced was uniformly spread over a PS medium plate (soluble starch 30 g/L, yeast extract 5 g/L, polypeptone 5 g/L, agar 20 g/L, adjusted to pH 7.0 with KOH) containing 12.5 µg/mL of tetracycline and the bacteria were cultured at 34° C. overnight. One-eighth of the bacterial cells on the plate were inoculated into 20 mL of fermentation medium in a 500 mL capacity Sakaguchi flask. Subsequently, calcium carbonate was added at 50 g/L and the bacteria were cultured at 34° C. with shaking. Sampling was conducted at 120 hours after the start of culturing, and the amounts of inosine and hypoxanthine in the culture medium were measured by conventional methods (Table 6). It was found that the strain with enhanced ribose-5-phosphate isomerase activity produced inosine more efficiently than the unmodified strain.

Composition of the fermentation medium:

| | |
|---|---|
| Glucose | 60 g/L |
| $KH_2PO_4$ | 1 g/L |
| $NH_4Cl$ | 32 g/L |
| Mameno (T-N)* | 1.35 g/L |
| Yeast extract | 1 g/L |
| DL-methionine | 0.3 g/L |
| L-tryptophan | 0.02 g/L |
| Adenine | 0.1 g/L |
| Guanosine | 0.075 g/L |
| $MgSO_4$ | 0.4 g/L |
| $FeSO_4$ | 0.01 g/L |
| $MnSO_4$ | 0.01 g/L |
| GD113 | 0.01 mL/L |
| (adjusted to pH 7.0 with KOH) | |
| Calcium carbonate | 50 g/L |

*Protein hydrolysis product

TABLE 6

| B. subtilis strain | OD610 | Residual glucose (g/L) | Inosine (g/L) | Inosine (%)*[1] |
|---|---|---|---|---|
| TABS100 | 8.4 | 0 | 5.77 | 18.73 |
| TABS102 | 9.8 | 1.3 | 5.96 | 20.21 |

*[1]Ratio of the produced inosine to the amount of the consumed glucose (g/g)

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing a purine-derived substance comprising:
   a) culturing a *Bacillus* bacterium in a medium; and
   b) collecting said purine-derived substance,
wherein said *Bacillus* bacterium is able to produce a purine-derived substance and has been modified to increase glucose-6-phosphate dehydrogenase activity by increasing the copy number of the gene encoding glucose-6-phosphate dehydrogenase or modifying an expression control sequence of the gene encoding glucose-6-phosphate dehydrogenase, wherein said glucose-6-phosphate dehydrogenase is selected from the group consisting of:
   (A) a protein comprising the amino acid sequence of SEQ ID No. 48, and
   (B) a modified protein comprising the amino acid sequence of SEQ ID No. 48 wherein one to 10 amino acids are substituted, deleted, inserted, or added, and said modified protein has glucose-6-phosphate dehydrogenase activity.

2. The method according to claim 1, wherein said purine-derived substance is a purine nucleoside or purine nucleotide.

3. The method according to claim 2, wherein said purine-derived substance is selected from the group consisting of inosine, xanthosine, guanosine, and adenosine.

4. The method according to claim 2, wherein said purine-derived substance is selected from the group consisting of inosinic acid, xanthylic acid, guanylic acid, and adenylic acid.

5. A method for producing a purine nucleotide comprising:
   a) producing a purine nucleoside by the method according to claim 3;
   b) reacting the purine nucleoside with a microorganism which is able to produce a nucleoside-5'-phosphate ester, or with an acid phosphatase, in the presence of a phosphate donor selected from the group consisting of phosphoric acid, phenyl phosphate, and carbamyl phosphate; and
   c) collecting the purine nucleotide.

6. The method according to claim 1, wherein the gene encoding said protein is selected from the group consisting of:
   (A) a DNA comprising the nucleotide sequence of SEQ ID NO: 47; and
   (B) a DNA that is able to hybridize with a nucleotide sequence complementary to the nucleotide sequence of SEQ ID NO: 47 under stringent conditions comprising washing at 1×SSC, and 0.1% SDS at 60° C., and wherein said DNA encodes a protein having glucose-6-phosphate hydrogenase activity.

7. The method according to claim 6, wherein said purine-derived substance is a purine nucleoside or purine nucleotide.

8. The method according to claim 6, wherein said purine-derived substance is selected from the group consisting of inosine, xanthosine, guanosine, and adenosine.

9. The method according to claim 6, wherein said purine-derived substance is selected from the group consisting of inosinic acid, xanthylic acid, guanylic acid, and adenylic acid.

10. The method according to claim 6, wherein the bacterium is further modified to overexpress a phosphoribosylpyrophosphate synthase gene.

11. The method according to claim 6, wherein the bacterium is further modified to enhance with the expression of the purine operon by disrupting a purR gene or deleting a portion of an attenuator region of the purine operon.

12. A method for producing a purine nucleotide comprising:
   a) producing a purine nucleoside by the method according to claim 8; and
   b) reacting the purine nucleoside with a microorganism which is able to produce a nucleoside-5'-phosphate ester or with an acid phosphatase in the presence of a phosphate donor selected from the group consisting of phosphoric acid, phenyl phosphate, and carbamyl phosphate; and
   c) collecting the purine nucleotide.

* * * * *